（12）United States Patent
Bhagat et al.

(10) Patent No.: US 11,510,619 B2
(45) Date of Patent: Nov. 29, 2022

(54) HEALTH AND VITAL SIGNS MONITORING RING WITH INTEGRATED DISPLAY AND MAKING OF SAME

(71) Applicant: Jabil Inc., St. Petersburg, FL (US)

(72) Inventors: Yusuf Abu Tayeb Bhagat, St. Petersburg, FL (US); Girish Satish Wable, St. Petersburg, FL (US); Patrick John Verdon, St. Petersburg, FL (US); Michael Nicholas Arfaras, St. Petersburg, FL (US); Thong Bui, St. Petersburg, FL (US); Krishnaveni Das, St. Petersburg, FL (US); Sai Guruva Reddy Avuthu, St. Petersburg, FL (US); Arnoldo Reta, St. Petersburg, FL (US); Jorg Richstein, St. Petersburg, FL (US)

(73) Assignee: Jabil Inc., St. Petersburg, FL (US)

( * ) Notice: Subject to any disclaimer, the term of this patent is extended or adjusted under 35 U.S.C. 154(b) by 153 days.

(21) Appl. No.: 16/711,663

(22) Filed: Dec. 12, 2019

(65) Prior Publication Data
US 2021/0177353 A1 Jun. 17, 2021

(51) Int. Cl.
*A61B 5/00* (2006.01)
*A61B 5/1455* (2006.01)
(Continued)

(52) U.S. Cl.
CPC ............ *A61B 5/6826* (2013.01); *A61B 5/01* (2013.01); *A61B 5/0245* (2013.01);
(Continued)

(58) Field of Classification Search
CPC ....... A61B 5/6826; A61B 5/1455; A61B 5/01; A61B 5/0245; A61B 2562/166; A61B 2562/0215; A61B 2562/0219
See application file for complete search history.

(56) References Cited

U.S. PATENT DOCUMENTS 3,049,406 A1 11/2011 Mackenzie et al.
9,711,060 B1 * 7/2017 Lusted .................. G09B 23/28
(Continued)

OTHER PUBLICATIONS

"Anas Albulbul, Evaluating Major Electrode Types of Idle Biological Signal Measurements for Modern Medical Technology, 2016, Department of Research and Development, Global Innovative Medical Technologies (GIMT)" (Year: 2016).*
(Continued)

*Primary Examiner* — Joseph M Dietrich
*Assistant Examiner* — Michael T. Holtzclaw
(74) *Attorney, Agent, or Firm* — Young Basile Hanlon & MacFarlane, P.C.

(57) ABSTRACT

A vital signs monitoring ring with integrated display includes a ring housing, the ring housing comprising at least two windows and a printed circuit board assembly (PCBA) layer configured to be attached to the ring housing. The PCBA layer includes a display section, a sensor section, a transmission mode oximetry measurement section configured to be in alignment with the at least two windows, a power supply, and a switch configured to power on the vital signs monitoring ring with integrated display via the power supply. The display section is configured to display physiological and action parameters associated with a user by sensing the physiological and action signals from a digit of user wearing the vital signs monitoring ring with integrated display using at least the sensor section and the transmission mode oximetry measurement section.

17 Claims, 18 Drawing Sheets

(51) Int. Cl.
*A61B 5/01* (2006.01)
*A61B 5/0245* (2006.01)

(52) U.S. Cl.
CPC .... *A61B 5/1455* (2013.01); *A61B 2562/0215* (2017.08); *A61B 2562/0219* (2013.01); *A61B 2562/0271* (2013.01); *A61B 2562/166* (2013.01)

(56) References Cited

U.S. PATENT DOCUMENTS

| | | | |
|---|---|---|---|
| 9,861,314 B2 | 1/2018 | Haverinen et al. | |
| D811,260 S | 2/2018 | Koskinen | |
| 10,182,750 B1 | 1/2019 | Philippine et al. | |
| 10,918,289 B1* | 2/2021 | Wasson | A61B 5/6826 |
| 2004/0087845 A1 | 5/2004 | Katarow et al. | |
| 2013/0096405 A1 | 4/2013 | Garfio | |
| 2015/0201875 A1* | 7/2015 | Tateda | A61B 5/72 600/324 |
| 2016/0015289 A1* | 1/2016 | Simon | A61B 5/7275 600/301 |
| 2017/0071483 A1* | 3/2017 | Wang | A61B 5/332 |
| 2017/0156651 A1 | 6/2017 | Arias et al. | |
| 2018/0020977 A1* | 1/2018 | Li | A61B 5/6826 600/384 |
| 2018/0042540 A1 | 2/2018 | Kinnunen et al. | |
| 2018/0279965 A1* | 10/2018 | Pandit | A61B 5/7225 |
| 2019/0022400 A1 | 1/2019 | Kumar et al. | |
| 2019/0029536 A1* | 1/2019 | Moon | A61B 5/681 |
| 2019/0204865 A1* | 7/2019 | Von Badinski | A61B 5/1455 |

OTHER PUBLICATIONS

"Timothy William Shay, Hydrogel and Microfluidic Enabling Technologies for Wearable Biomonitoring Devices: Sweat and ECG Sensing, 2017, ProQuest Dissertations Publishing" (Year: 2017).*
Lochner et al. "All-organic optoelectronic sensor for pulse oximetry," Nature Communications, vol. 5, p. 5745, Dec. 10, 2014.
Park et al "Real-Time Heart Monitoring System based on Ring-Type Pulse Oximeter Sensor," Journal of Electrical Engineering and Technology, vol. 8, No. 2, pp. 376-384, Mar. 2013.
Yokota et al "Ultraflexible organic photonic skin," Science Advances, Apr. 15, 2016.
Khan et al "A flexible organic reflectance oximeter array," PNAS, vol. 115, No. 47, Nov. 7, 2018.
Khan et al "System Design for Organic Pulse Oximeter," Advances in Sensors and Interfaces, IWASI, Aug. 2015.
Khan et al "Supplementary Information for a flexible organic reflectance oximeter array," PNAS, pp. 1-20 https://www.pnas.org/content/suppl/2018/11/06/1813053115.DCSupplemental, retrieved Oct. 2018.

* cited by examiner

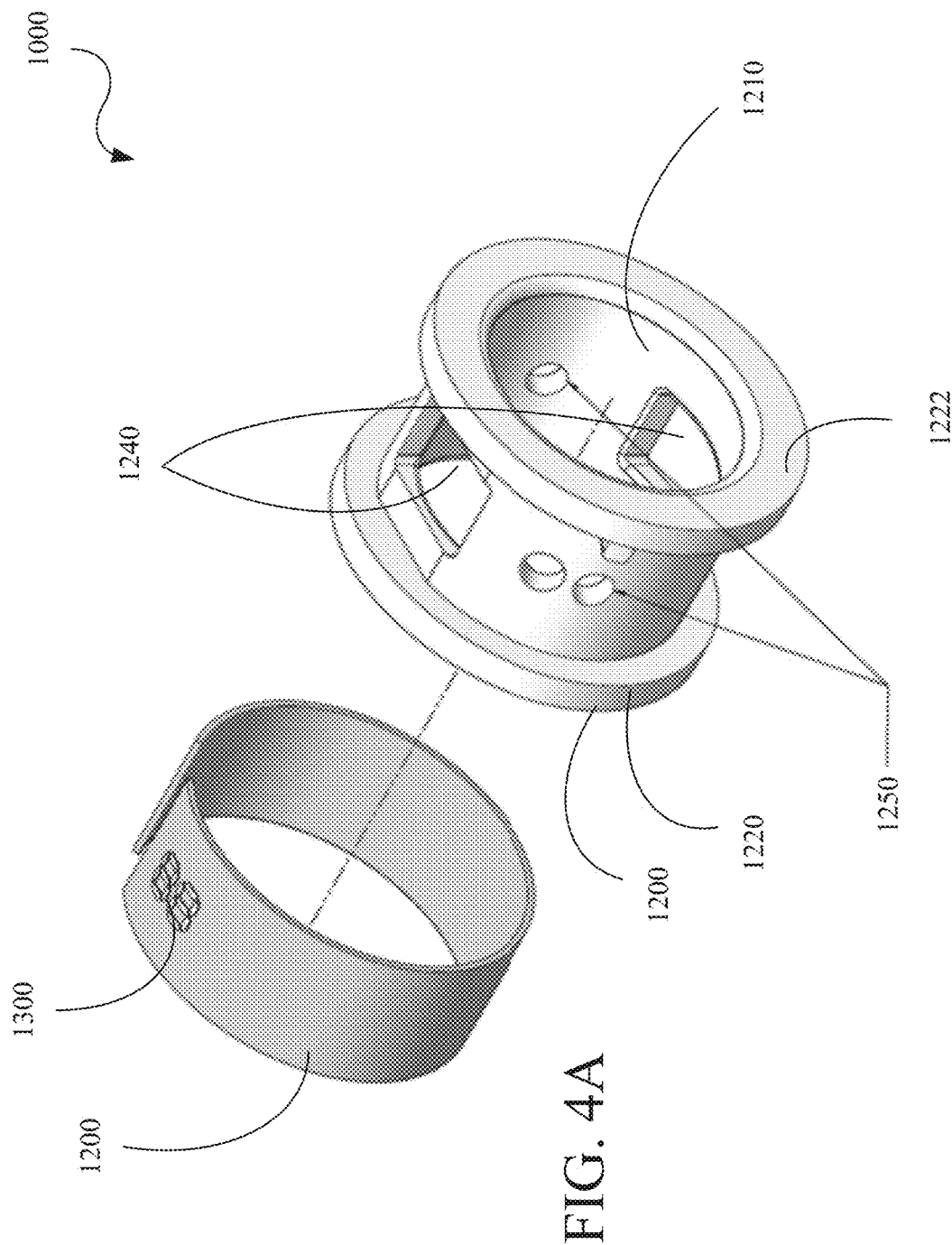

HEALTH AND VITAL SIGNS MONITORING RING WITH INTEGRATED DISPLAY AND MAKING OF SAME

TECHNICAL FIELD

This disclosure relates to electronics and in particular, a ring for monitoring and displaying health signs, vital signs, and the like with an integrated display.

BACKGROUND

Vital signs monitoring devices are capable of measuring multiple physiologic parameters of a patient. These physiologic parameters may include heart rate, electrocardiogram (ECG) signals, photoplethysmography (PPG) signals, and other like signals and information. The vital sign monitoring devices come in a variety of forms including smart watches, wearable devices, and the like. The use of such devices has become ubiquitous as users become more health conscious. The devices may be used in a variety of settings including medical facilities, home, and work, and while walking, exercising and performing other activities. The devices, however, lack depicting the multi-parametric measurements associated with the multiple sensing modalities on the devices such as ECG, oxygen saturation, temperature and pH, for example. In addition, the devices may be costly, need maintenance, and may be difficult to use or interpret. Consequently, there is a need for an easy to use vital signs monitoring device which may be more suitable and adaptable for a variety of environments.

SUMMARY

Disclosed herein are implementations of health and/or vital signs monitoring ring with integrated display and methods for making the rings or devices.

In implementations, a vital signs monitoring ring with integrated display includes a ring housing, the ring housing comprising at least two windows and a printed circuit board assembly (PCBA) layer configured to be attached to the ring housing. The PCBA layer includes a display section, a sensor section, a transmission mode oximetry measurement section configured to be in alignment with the at least two windows, a power supply, and a switch configured to power on the vital signs monitoring ring with integrated display via the power supply. The display section is configured to display physiological and action parameters associated with a user by sensing the physiological and action signals from a digit of user wearing the vital signs monitoring ring with integrated display using at least the sensor section and the transmission mode oximetry measurement section.

In implementations, a vital signs monitoring ring with integrated display includes a first layer having a display section and an activation switch, a second layer having a sensor section and a power supply, and a third layer having an oximetry sensor. The first layer, the second layer, and the third layer are electrically and mechanically connected and collectively configured to be in a cylindrical configuration, where activation of the activation switch powers on the vital signs monitoring ring with integrated display via the power supply, and the display section is configured to display physiological and action parameters associated with a user by sensing the physiological and action signals from a digit of user wearing the vital signs monitoring ring with integrated display using at least the sensor section and the oximetry sensor.

In implementations, a vital signs monitoring ring with integrated display includes a display layer including a switch and a sensor layer including at least accelerometer, a temperature sensor, and a transmission mode oximetry sensor. The display layer and the sensor layer are electrically and mechanically connected and collectively configured to be in a cylindrical configuration, where activation of an activation switch powers on the vital signs monitoring ring with integrated display via a power supply, and the display section is configured to display sensor data associated with a user by sensing signals from a digit of user wearing the vital signs monitoring ring with integrated display using at least the accelerometer, the temperature sensor, and the transmission mode oximetry sensor.

BRIEF DESCRIPTION OF THE DRAWINGS

The disclosure is best understood from the following detailed description when read in conjunction with the accompanying drawings and are incorporated into and thus constitute a part of this specification. It is emphasized that, according to common practice, the various features of the drawings are not to-scale. On the contrary, the dimensions of the various features are arbitrarily expanded or reduced for clarity.

FIGS. 4A-B are perspective views of a printed circuit board assembly (PCBA) and an outer shell of the vital signs monitoring ring with integrated display of FIG. 1 in accordance with certain implementations.

DETAILED DESCRIPTION

Figure 1:
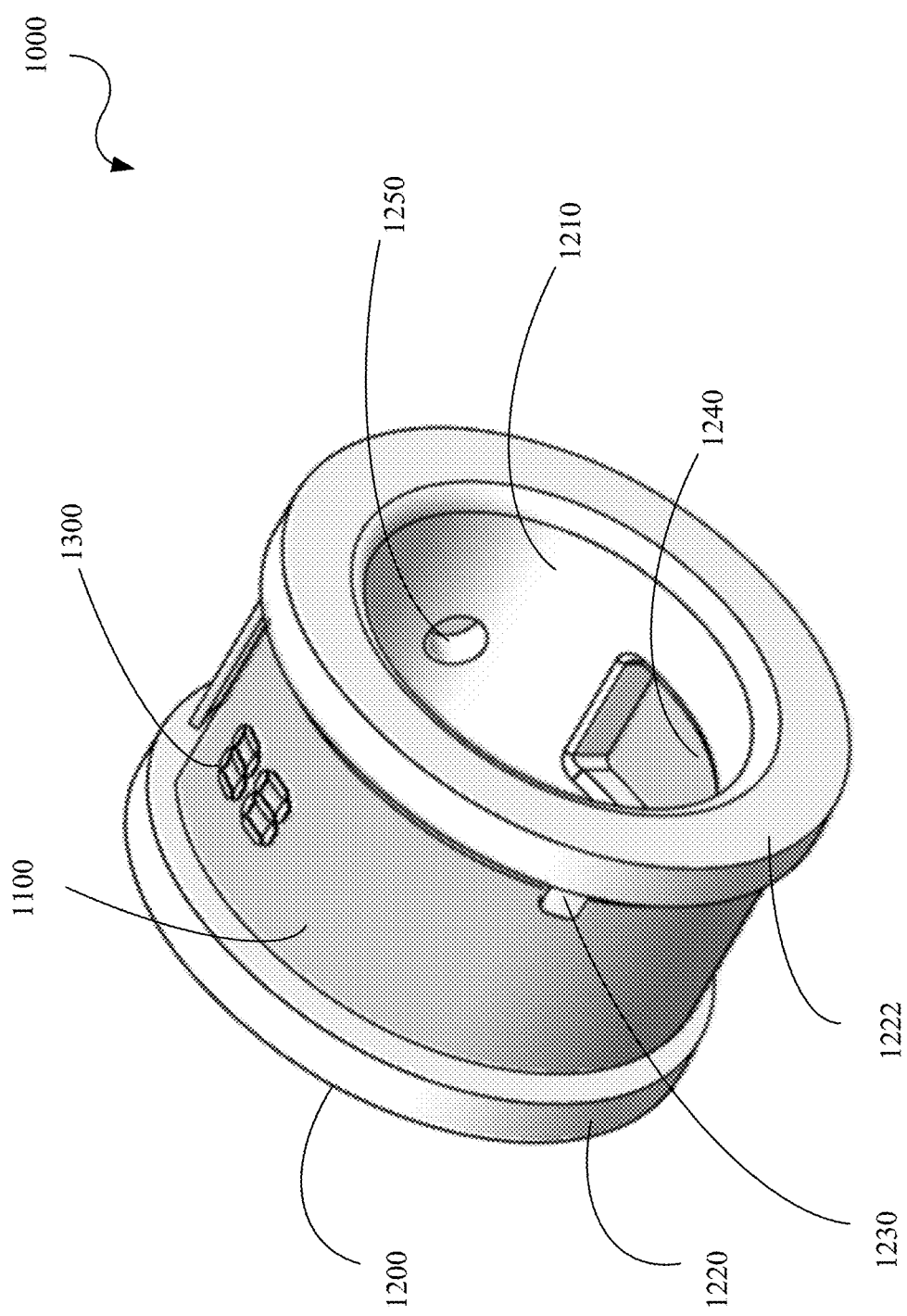
FIG. 1 is a perspective view of an example vital signs monitoring ring with integrated display in accordance with certain implementations.

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical similar devices, systems, compositions and methods. Those of ordinary skill may thus recognize that other elements and/or steps may be desirable or necessary to implement the devices, systems, compositions and methods described herein. However, because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art in light of the discussion herein.

Embodiments are provided throughout so that this disclosure is sufficiently thorough and fully conveys the scope of the disclosed embodiments to those who are skilled in the art. Numerous specific details are set forth, such as examples of specific aspects, devices, and methods, to provide a thorough understanding of embodiments of the present disclosure. Nevertheless, it will be apparent to those skilled in the art that certain specific disclosed details need not be employed, and that embodiments may be embodied in different forms. As such, the exemplary embodiments set forth should not be construed to limit the scope of the disclosure.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, steps, operations, elements, and/or components, but do not preclude the presence or addition of one or more other features, steps, operations, elements, components, and/or groups thereof.

The steps, processes, and operations described herein are thus not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

Yet further, although the terms first, second, third, etc. may be used herein to describe various elements, steps or aspects, these elements, steps or aspects should not be limited by these terms. These terms may be only used to distinguish one element or aspect from another. Thus, terms such as "first," "second," and other numerical terms when used herein do not imply a sequence or order unless clearly indicated by the context. Thus, a first element, step, component, region, layer or section discussed below could be termed a second element, step, component, region, layer or section without departing from the teachings of the disclosure.

As used herein, the terminology "determine" and "identify," or any variations thereof includes selecting, ascertaining, computing, looking up, receiving, determining, establishing, obtaining, or otherwise identifying or determining in any manner whatsoever using one or more of the devices and methods are shown and described herein.

As used herein, the terminology "example," "the embodiment," "implementation," "aspect," "feature," or "element" indicates serving as an example, instance, or illustration. Unless expressly indicated, any example, embodiment, implementation, aspect, feature, or element is independent of each other example, embodiment, implementation, aspect, feature, or element and may be used in combination with any other example, embodiment, implementation, aspect, feature, or element.

As used herein, the terminology "or" is intended to mean an inclusive "or" rather than an exclusive "or." That is unless specified otherwise, or clear from context, "X includes A or B" is intended to indicate any of the natural inclusive permutations. That is if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from the context to be directed to a singular form.

As used herein, the terminology "computer" or "computing device" includes any unit, or combination of units, capable of performing any method, or any portion or portions thereof, disclosed herein. For example, the "computer" or "computing device" may include at least one or more processor(s).

As used herein, the terminology "processor" indicates one or more processors, such as one or more special purpose processors, one or more digital signal processors, one or more microprocessors, one or more controllers, one or more microcontrollers, one or more application processors, one or more central processing units (CPU)s, one or more graphics processing units (GPU)s, one or more digital signal processors (DSP)s, one or more application specific integrated circuits (ASIC)s, one or more application specific standard products, one or more field programmable gate arrays, any other type or combination of integrated circuits, one or more state machines, or any combination thereof.

As used herein, the terminology "memory" indicates any computer-usable or computer-readable medium or device that can tangibly contain, store, communicate, or transport any signal or information that may be used by or in connection with any processor. For example, a memory may be one or more read-only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof.

As used herein, the terminology "instructions" may include directions or expressions for performing any method, or any portion or portions thereof, disclosed herein, and may be realized in hardware, software, or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

As used herein, the term "application" refers generally to a unit of executable software that implements or performs one or more functions, tasks or activities. For example, applications may perform one or more functions including, but not limited to, vital signs monitoring, health monitoring, telephony, web browsers, e-commerce transactions, media players, travel scheduling and management, smart home management, entertainment, and the like. The unit of executable software generally runs in a predetermined environment and/or a processor.

The non-limiting embodiments described herein are with respect to rings or devices and methods for making the rings or devices, where the rings or devices are vital signs monitoring or health signs monitoring rings or devices with integrated display. The ring or device and method for making the ring or device with integrated display may be modified for a variety of applications and uses while remaining within the spirit and scope of the claims. The embodiments and variations described herein, and/or shown in the drawings, are presented by way of example only and are not limiting as to the scope and spirit. The descriptions herein may be applicable to all embodiments of the device and the methods for making the devices.

Disclosed herein are implementations of health or vital (collectively "vital") signs monitoring rings or devices with integrated display (collectively "rings") and methods for making the rings. The vital signs monitoring ring with integrated display is easily attached and removed from the user. The rings may use a combination of sensors, printed electronics, batteries, display electronics, flexible materials or enclosures. In an implementation, the vital signs monitoring ring with integrated display includes flexible display layers based on organic, electrochromic, or quantum dot display techniques and materials. The parameters that may be displayed on the ring include, but are not limited to, heart rate (HR), heart rate variability (HRV), oxygen saturation ($SpO_2$), body surface temperature, pH levels and the like.

The vital signs monitoring ring with integrated display integrates multiple sensing modalities such as, but not limited to, photoplethysmography (PPG), oxygen saturation mapping (oximetry), temperature monitoring, and pH monitoring in one wearable device for detecting pulsatile signals or the lack thereof. In an implementation, the vital signs monitoring ring with integrated display may include a single or multi-lead electrocardiogram (ECG) sensor. The device and captured data are used to track the data from the multiple sensing modalities over time. In an implementation, the vital signs monitoring ring with integrated display is reusable and rechargeable.

In an implementation, the variety of sensors may include, but is not limited to, a PPG sensor, temperature sensors, and an accelerometer. In an implementation, the PPG sensor is a transmission mode oximetry measurement sensor. In an implementation, the transmission mode oximetry measurement sensor may include light emitting diodes (LEDs) and photodiodes. The LEDs may be red LEDs, near infrared (NIR) LEDs, and/or green LEDs. In an implementation, the vital signs monitoring ring with integrated display may include a single lead ECG sensor.

In an implementation, the vital signs monitoring ring with integrated display may include a low power microcontroller with Bluetooth® for communication, an analog front-end (AFE) for measuring oximetry signals (PPG) and oxygen saturation ($SpO_2$), an accelerometer, temperature sensor, and an oximetry layer including LEDs and photodiodes. In an implementation, the LEDs and photodiodes are on the same layer and same plane. In this instance, oximetry measurement is done via reflection or reflective oximetry. In an implementation, the LEDs and photodiodes are on the same layer and on different planes. In this instance, oximetry measurement is done via transmissive oximetry. In an implementation, a combination of reflective and transmissive can be done by appropriate placement of the LEDs and photodiodes. In an implementation, the AFE of the vital signs monitoring ring with integrated display may measure ECG signals and the vital signs monitoring ring with integrated display may include screen printed Silver-Silver Chloride electrodes (Ag—AgCl). In an implementation, the vital signs monitoring ring with integrated display may include a pH sensor.

Power for the ring is internally supplied by a battery or power source as described herein. The battery provides power to the various components on the vital signs monitoring ring with integrated display. The battery may permit the vital signs monitoring ring with integrated display to be run in a continuous mode of operation for a defined time period. For example, the defined time period may be 7 days. In an implementation, the battery may be a stack of Lithium polymer or similar batteries providing 3.6 V and 50 mAh, for example. In implementations, the battery is a flexible battery. In implementations, the battery is a rigid battery. In implementations, the battery is a flexi-rigid battery.

The data from the vital signs monitoring ring with integrated display may be communicated to a mobile device for display or analysis. In an implementation, the communication may be done via wireless, Bluetooth®, and the like. The data may include ECG live data, heart rate, heart rate variability, fall detection, $SpO_2$, pH, body surface temperature, and the like. In an implementation, the flexible battery is rechargeable.

Figure 2:
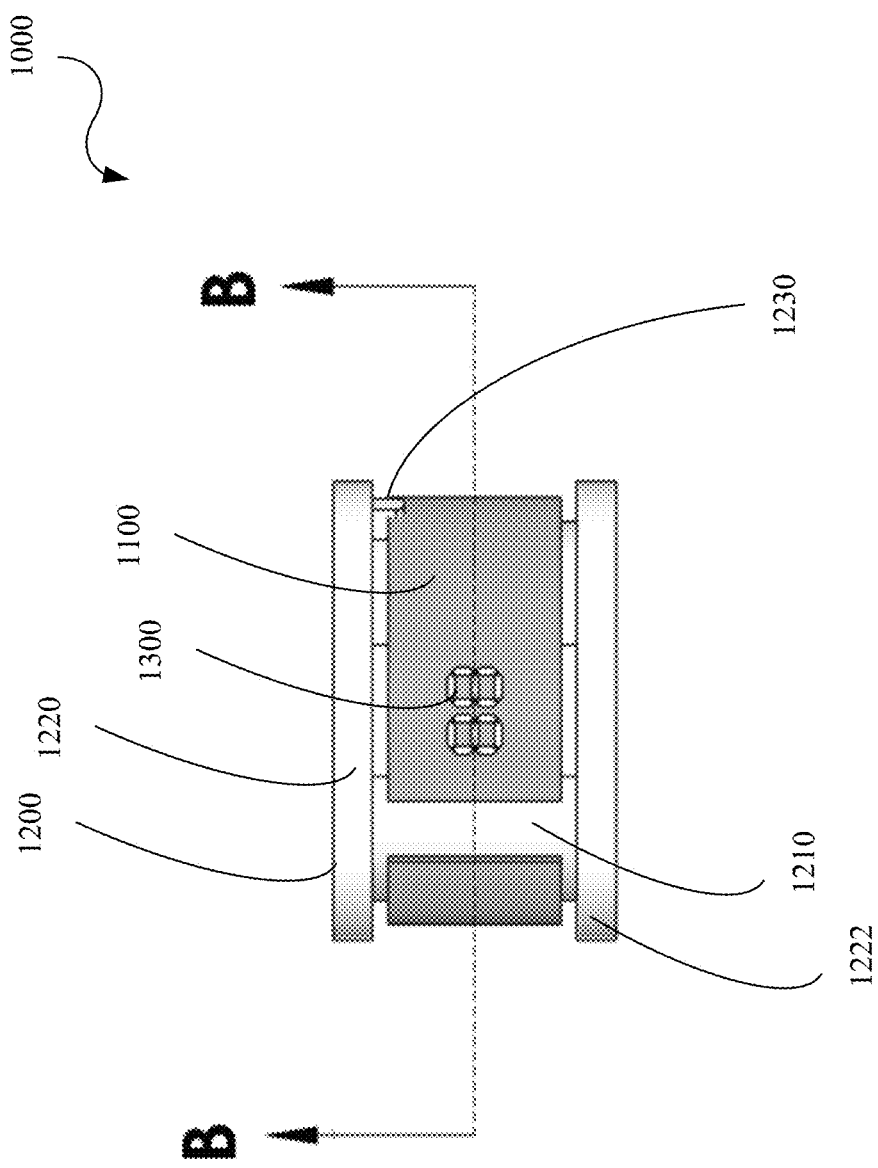
FIG. 2 is a top view of the vital signs monitoring ring with integrated display of FIG. 1 in accordance with certain implementations.
Figure 3:
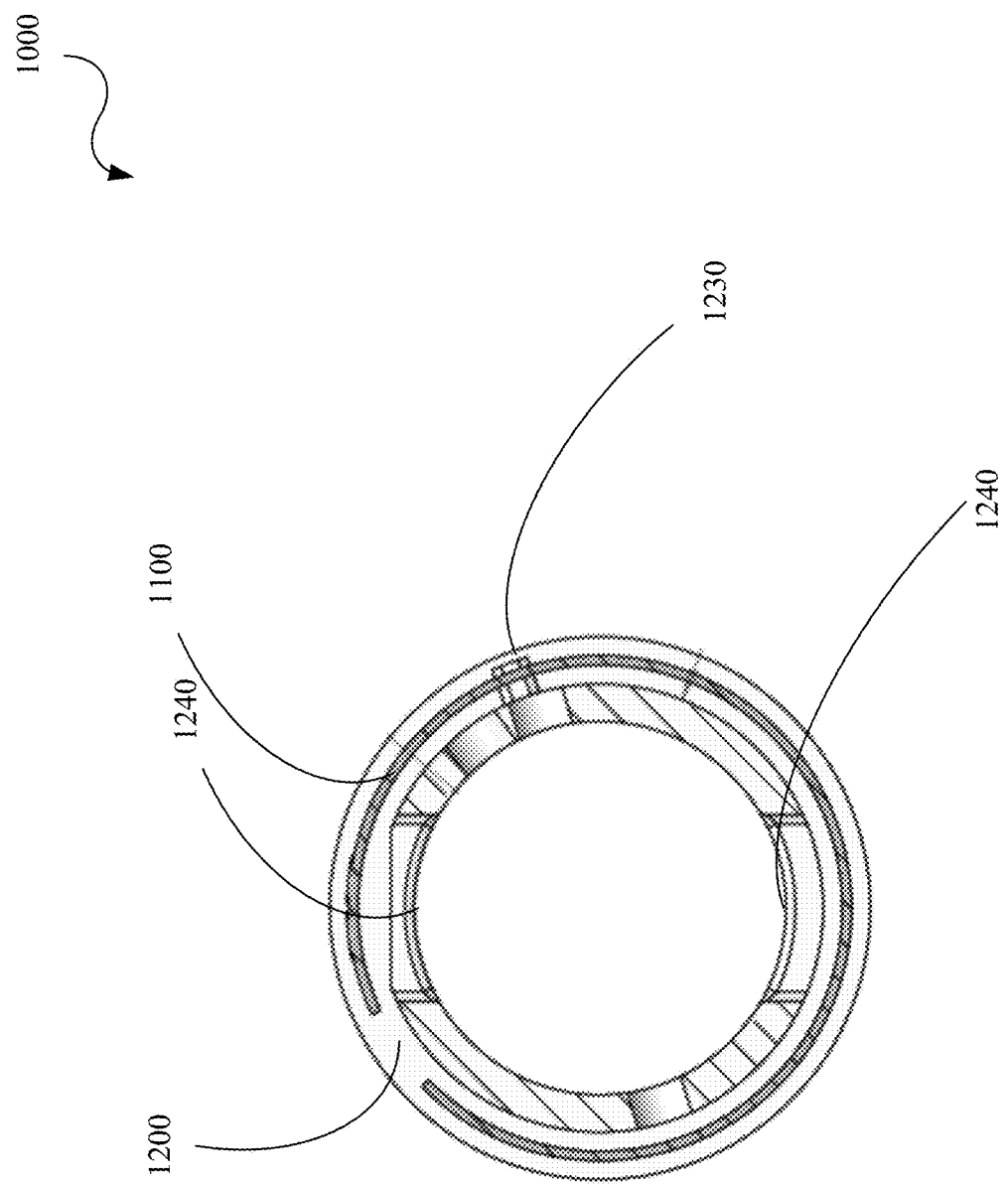
FIG. 3 is a cross-sectional view along line B-B of the vital signs monitoring ring with integrated display of FIG. 1 in accordance with certain implementations.

FIG. 1 is a perspective view of an example vital signs monitoring ring with integrated display 1000 in accordance with certain implementations, FIG. 2 is a top view of the vital signs monitoring ring with integrated display 1000 in accordance with certain implementations, FIG. 3 is a cross-sectional view along line B-B of the vital signs monitoring ring with integrated display 1000 in accordance with certain implementations, and FIGS. 4A-B are perspective views of a printed circuit board assembly (PCBA) layer 1100 and a ring shell 1200 of the vital signs monitoring ring with integrated display 1000 in accordance with certain implementations. In an implementation, the PCBA layer 1100 is configured to be cylindrically positioned on and attached to the ring shell 1200. In an implementation, the PCBA layer 1100 is configured to be cylindrically positioned on and bonded to the ring shell 1200.

The vital signs monitoring ring with integrated display 1000 includes the PCBA layer 1100 and the ring shell 1200. As shown and described herein, the PCBA layer 1100 may be a flexible double surface populated PCBA. In an implementation, the PCBA layer 1100 may include a display area 1300. In an implementation, the display area 1300 may be a 2-digit, 7-segment display. In an implementation, the display area 8110 may have more or less digits. In an implementation, the display area 1300 may be a printed display. In an implementation, the display area 1300 may be a printed LED display implemented using organic, electrochromic, or quantum dot display techniques and materials as described herein. In an implementation, the display area 1300 may display oxygen saturation, pH levels, temperature, heart rate, and other physiological parameters. In an implementation, the display area 1300 may include step counts and other action-related parameters. In an implementation, the display area 1300 may include multiple display areas, where each display area may display a different physiological or action-related parameter.

In an implementation, the PCBA layer 1100 may include a pair of printed silver-silver chloride (Ag—AgCl) electrodes for an ECG sensor measurements or for other sensor measurements. In an implementation, the electrodes are screen-printed Ag—AgCl electrodes. In an implementation, there is one electrode one each surface of the PCBA layer 1100, where a first electrode contacts a user surface when the vital signs monitoring ring with integrated display 1000 is positioned on a user digit and a second electrode is touchable or engageable by a user to complete a sensor circuit with the first electrode. In an implementation, the first electrode contacts the user surface via a hydrogel layer.

In an implementation, the PCBA layer 1100 may include a variety of sensors (as shown and described herein) including, but not limited to, PPG sensor, ECG sensor, an accelerometer, pH sensor, and temperature sensor(s). In an implementation, the accelerometer may be used for activity tracking such as steps, fall detection, sleep efficiency, and sleep staging. In an implementation, one or more temperature sensors may be used to determine a temperature profile for a wound, for example. The one or more temperature sensors may sense or monitor surface temperatures of a localized body area. In an implementation, the pH sensor may monitor the pH levels of a localized body area. The pH level may vary from 0 to 14 and as stated herein, may be displayed via layer 1. For example, pH of normal healing wounds range from 5.5 to 6.5 and pH of nonhealing wounds are greater than 6.5. In an implementation, the pH sensors may be potentiometric pH sensors. In an implementation, the pH sensors may be implemented using carbon/polyaniline and Ag—AgCl electrodes.

In an implementation, the ring shell 1200 may have a spool or spindle type form including a cylinder 1210 having a pair of rims or ridges 1220 and 1222 at each end of the cylinder 1210. In an implementation, the cylinder 1210 may include tabs or projections 1230 for maintaining the PCBA layer 1100 on the cylinder 1210. In an implementation, the cylinder 1210 may include windows 1240 for operation of sensors on the PCBA layer 1100 as described herein. For example, the windows 1240 may allow light transmissions from light emitting diodes (LEDs) to impact a user surface and be detected by photodiodes after traveling through a user digit or the like. In an implementation, the cylinder 1210 may include charging ports 1250 for charging and recharging the vital signs monitoring ring with integrated display 1000. In an implementation, the ring shell 1200 may be flexi-rigid. In an implementation, the ring shell 1200 may be rigid. In an implementation, the ring shell 1200 may be flexible.

Figure 5A:
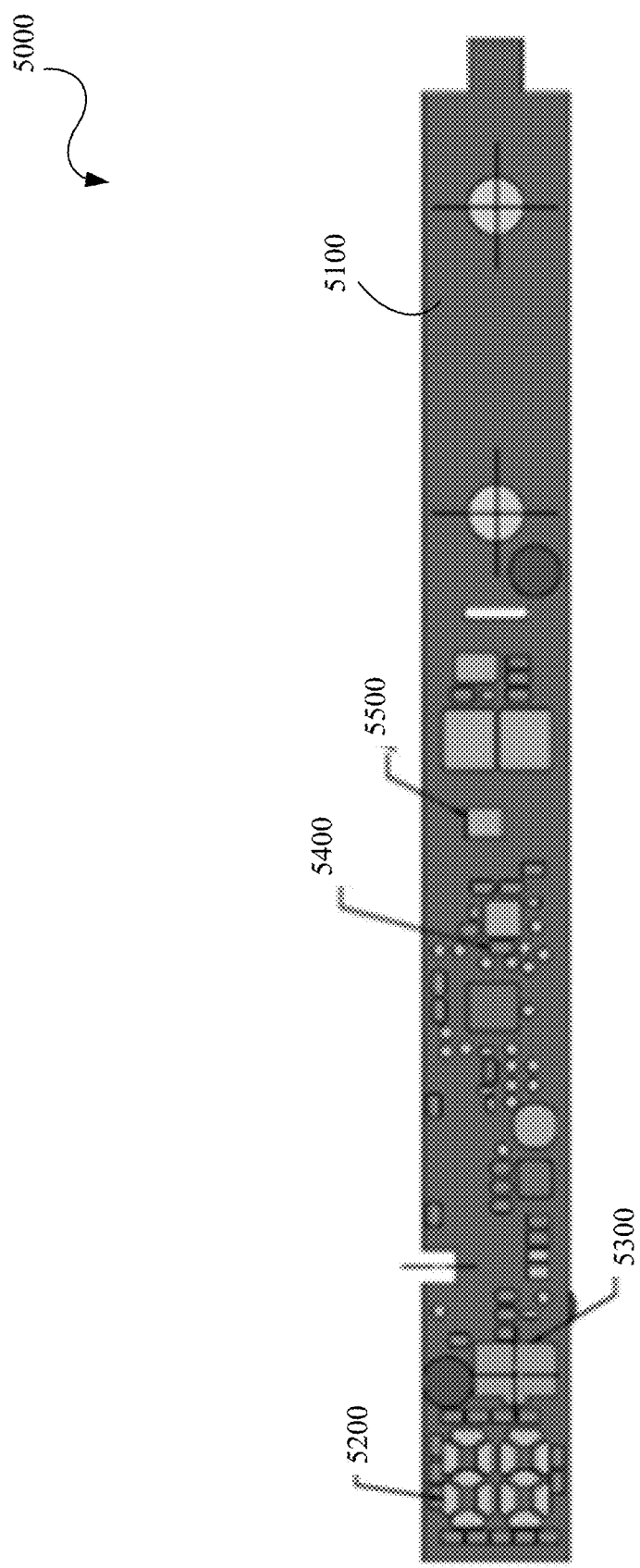
FIG. 5A is a top view or outer surface of a PCBA for a vital signs monitoring ring with integrated display in accordance with certain implementations.
Figure 5B:
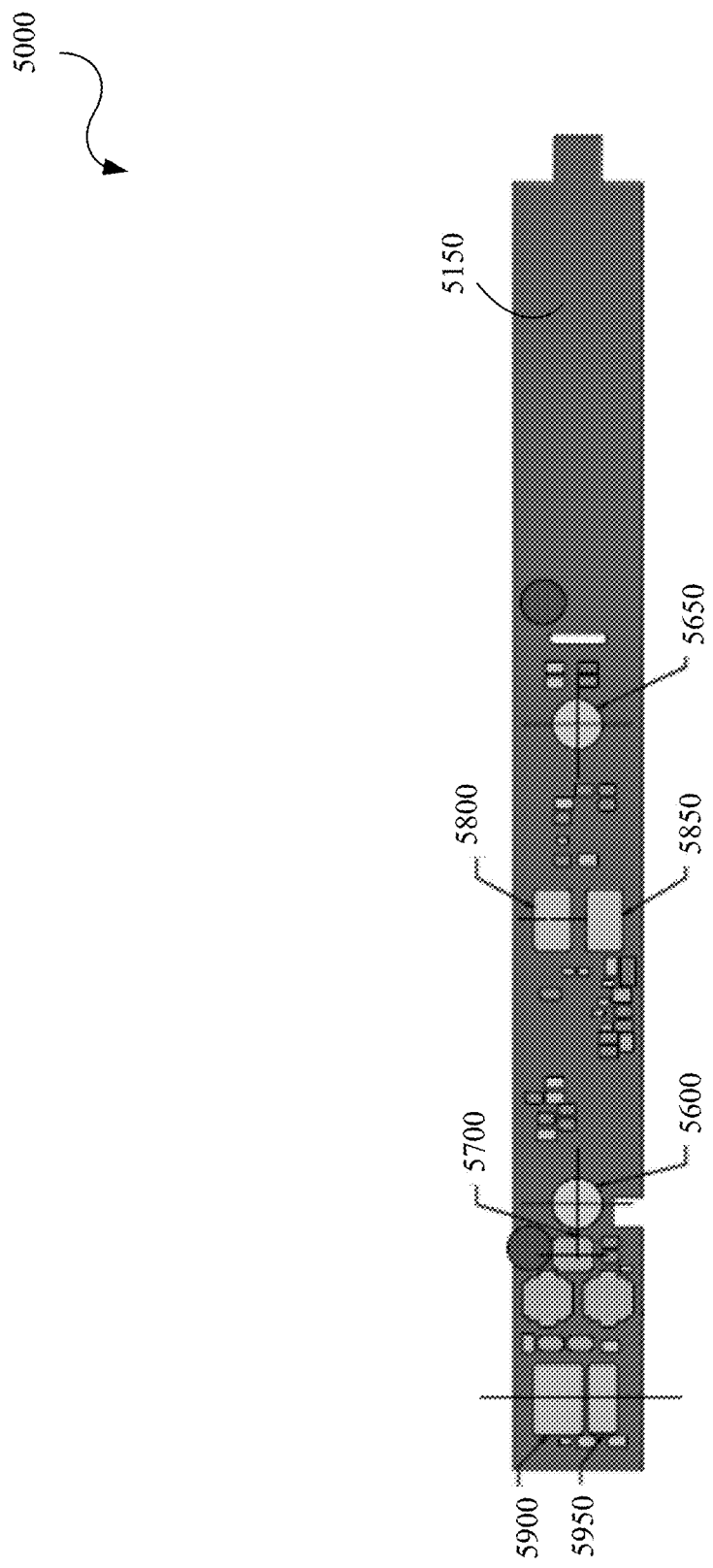
FIG. 5B is a bottom view or inner surface of the PCBA of FIG. 5A in accordance with certain implementations.
Figure 5C:
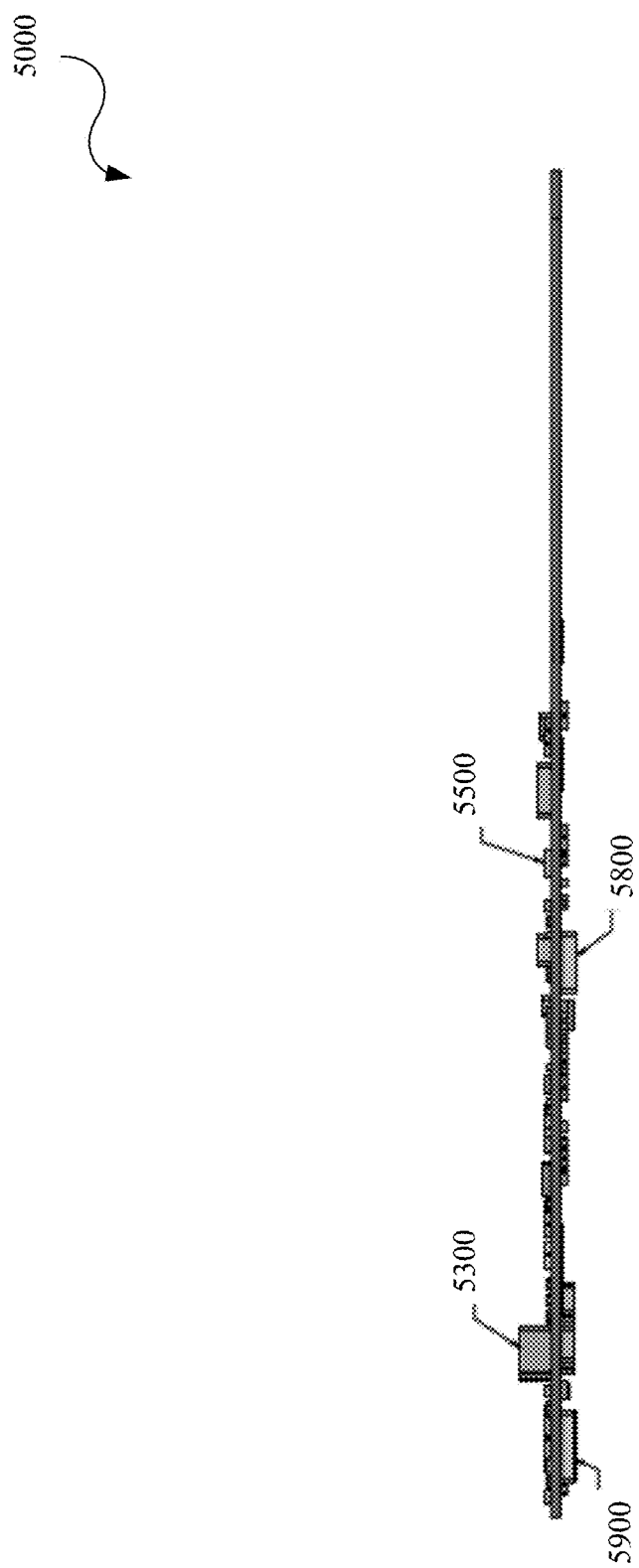
FIG. 5C is a side view of the PCBA of FIG. 5A in accordance with certain implementations.

FIG. 5A is a top view or outer surface 5100 of a PCBA layer 5000 for a vital signs monitoring ring with integrated display in accordance with certain implementations. The outer surface 5100 of the PCBA layer 5000 may include a display section 5200, a switch 5300, an accelerometer 5400, an analog front-end 5500, and other components. In an implementation, the display section 5200 may be a segmented LED display which includes a plurality of LEDs. FIG. 5B is a bottom view or inner surface 5150 of the PCBA layer 5000 of FIG. 5A in accordance with certain implementations. The inner surface 5150 of the PCBA layer 5000 may include charging terminals 5600 and 5650, temperature sensor 5700, photodiodes 5800 and 5850, sensor LEDs 5900 and 5950, and other components. FIG. 5C is a side view of the PCBA layer 5000 of FIG. 5A in accordance with certain implementations. The side view of the PCBA layer 5000 may show the switch 5300, the analog front-end 5500, the photodiode 5800, the sensor LEDs 5900, and other components. The PCBA layer 5000 and the components shown herein function as described herein in the specification.

Figure 6:
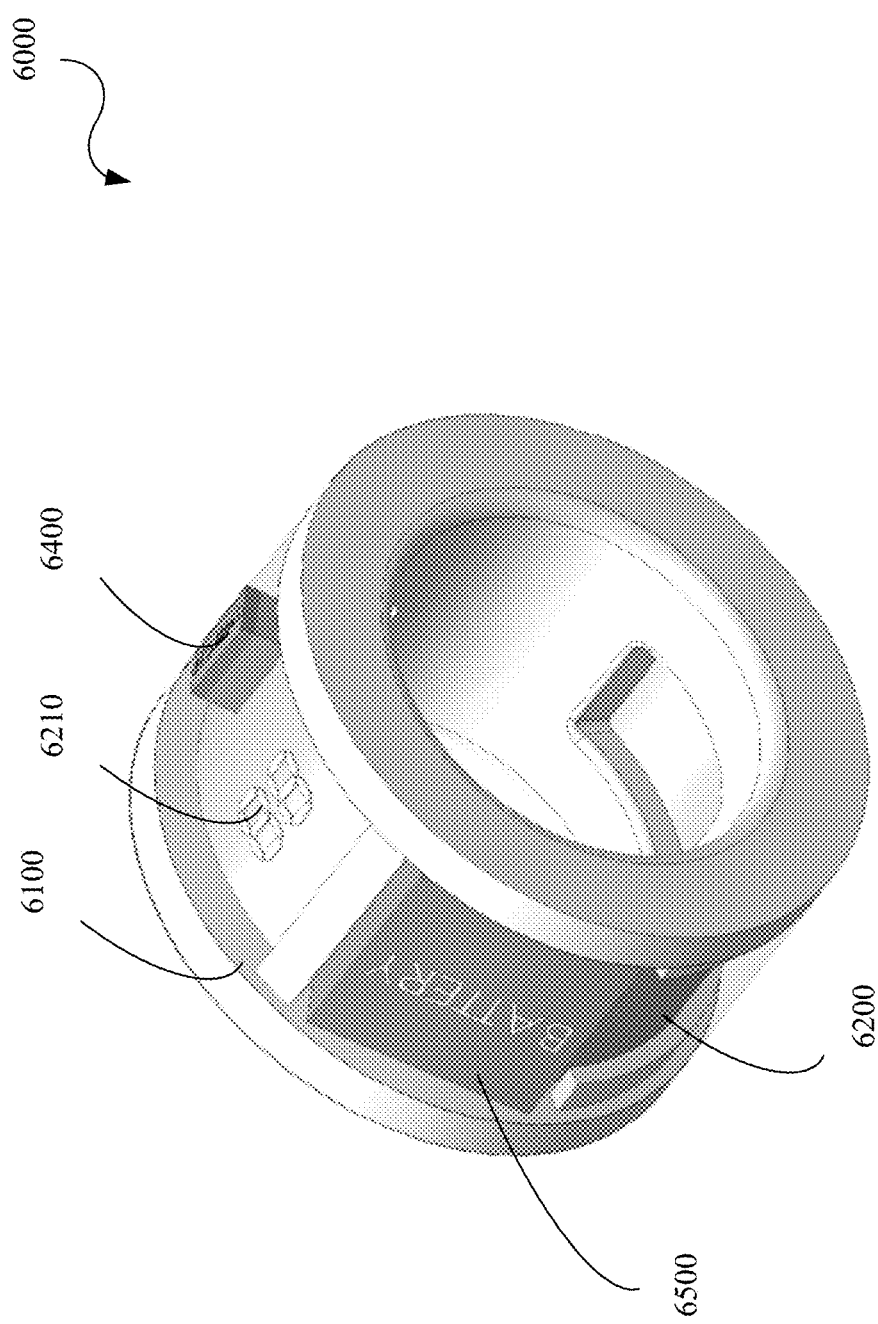
FIG. 6 is a perspective view of an example vital signs monitoring ring with integrated display in accordance with certain implementations.
Figure 7:
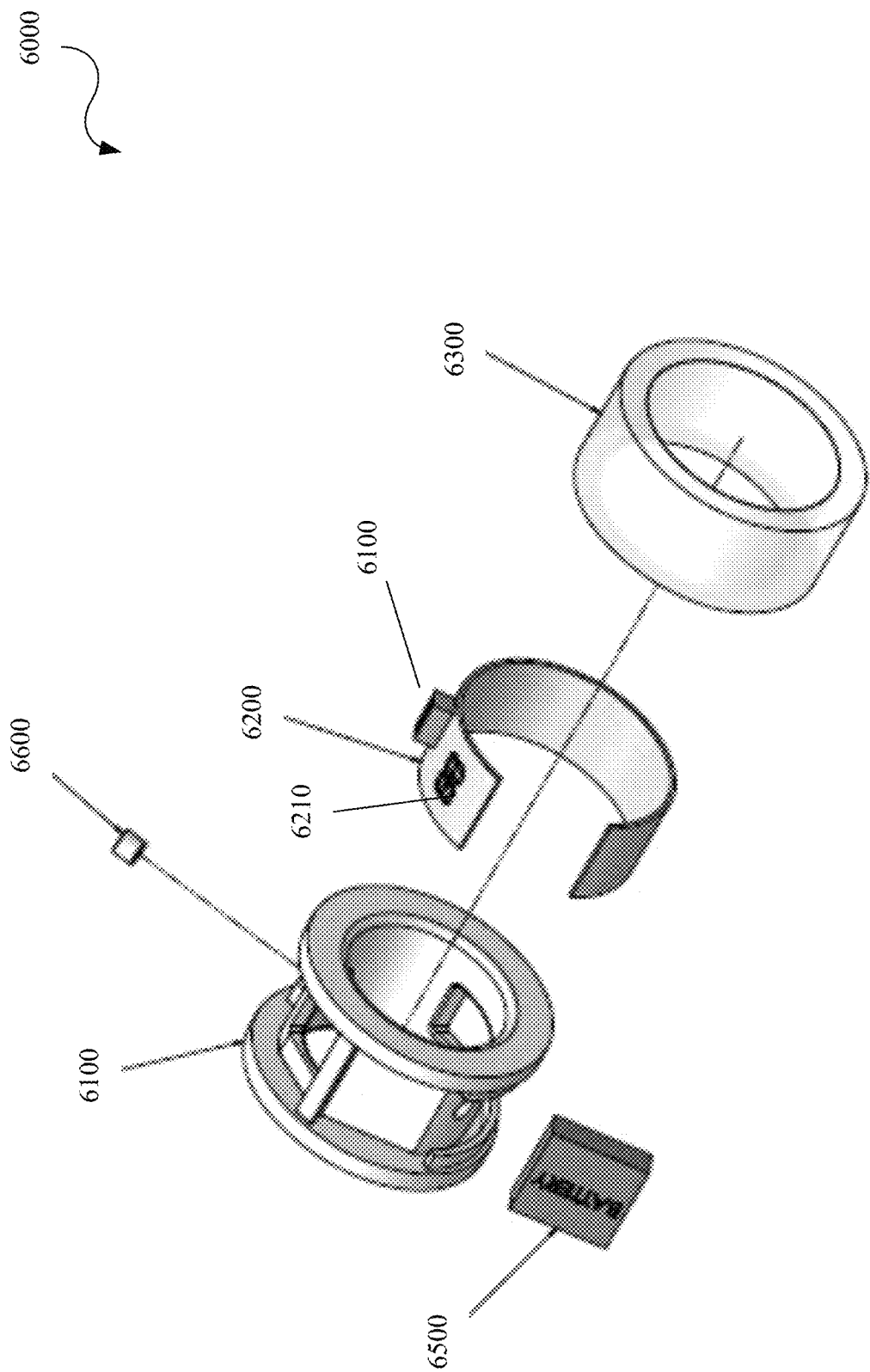
FIG. 7 is an exploded perspective view of the vital signs monitoring ring with integrated display of FIG. 6 in accordance with certain implementations.

FIG. 6 is a perspective view of an example vital signs monitoring ring with integrated display 6000 in accordance with certain implementations. FIG. 7 is an exploded perspective view of the vital signs monitoring ring with integrated display 6000 of FIG. 6 in accordance with certain implementations. The vital signs monitoring ring with integrated display 6000 includes a ring shell 6100, a PCBA layer 6200, and an overmold layer 6300. As shown and described herein, the PCBA layer 6200 may be a flexible double surface populated PCBA. A switch 6400 is connected to the PCBA layer 6200 and a battery 6500 is attached to the ring shell 6100 and connected to the PCBA layer 6200. The ring shell 6100 and the PCBA layer 6200 and components function as described herein in the specification. For example, the PCBA layer 6200 may include a variety of sensors (as shown and described herein) including, but not limited to, a temperature sensor 6600. The overmold layer 6300 covers the ring shell 6100, the PCBA layer 6200, and the battery 6500, and provides access to the switch 6400.

In an implementation, the PCBA layer 6200 may include a display area 6210. In an implementation, the display area 6210 may be a 2-digit, 7-segment display. In an implementation, the display area 6210 may have more or less digits. In an implementation, the display area 6210 may be a printed display. In an implementation, the display area 6210 may be a printed LED display implemented using organic, electrochromic, or quantum dot display techniques and materials as described herein. In an implementation, the display area 6210 may display oxygen saturation, pH levels, temperature, heart rate, and other physiological parameters. In an implementation, the display area 6210 may include step counts and other action-related parameters. In an implementation, the display area 6210 may include multiple display areas, where each display area may display a different physiological or action-related parameter.

Figure 8B:
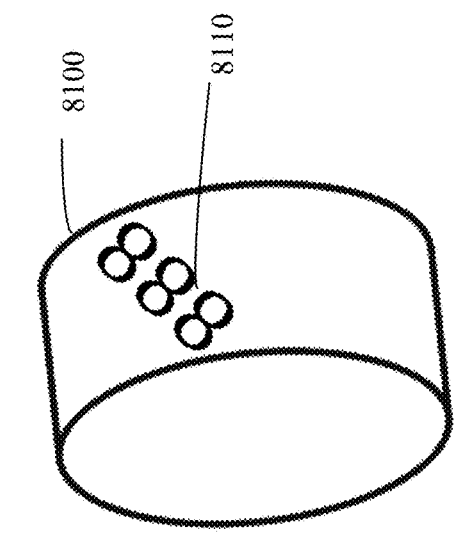
FIG. 8B is a perspective view of an outer layer of the vital signs monitoring ring with integrated display of FIG. 8A in accordance with certain implementations.
Figure 8C:
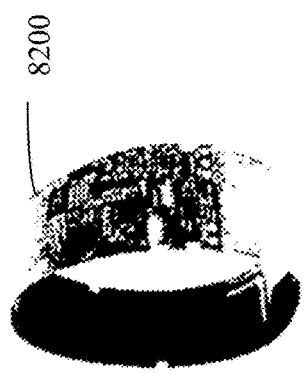
FIG. 8C is a perspective view of a PCBA layer of the vital signs monitoring ring with integrated display of FIG. 8A in accordance with certain implementations.
Figure 8D:
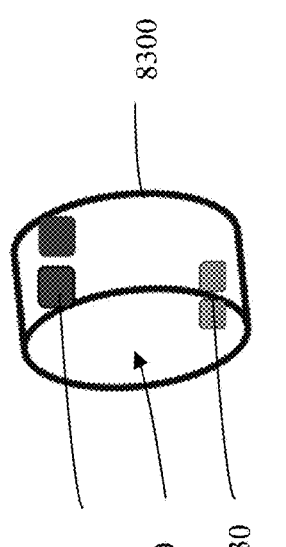
FIG. 8D is a perspective view of an inner layer of the vital signs monitoring ring with integrated display of FIG. 8A in accordance with certain implementations.
Figure 8A:
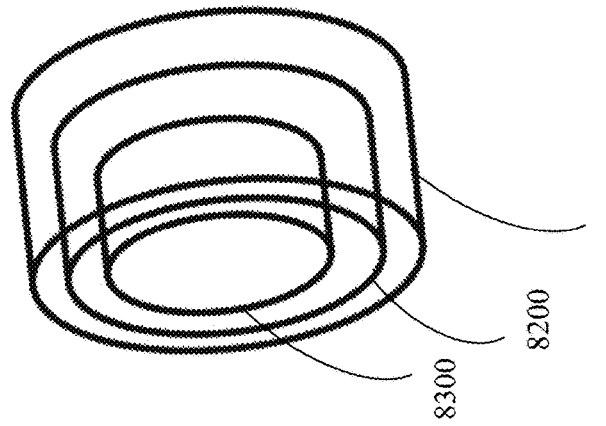
FIG. 8A is a perspective view of a vital signs monitoring ring with integrated display in accordance with certain implementations.

FIG. 8A is a perspective view of a vital signs monitoring ring with integrated display 8000 in accordance with certain implementations, FIG. 8B is a perspective view of an outer layer 8100 of the vital signs monitoring ring with integrated display 8000 in accordance with certain implementations, FIG. 8C is a perspective view of a PCBA layer 8200 of the vital signs monitoring ring with integrated display 8000 in accordance with certain implementations, and FIG. 8D is a perspective view of an inner layer 8300 of the vital signs monitoring ring with integrated display 8000 in accordance with certain implementations. In an implementation, the vital signs monitoring ring with integrated display 8000 may include a ring structure for holding or housing the outer layer 8100, the PCBA layer 8200, and the inner layer 8300 such as, for example, the ring shell 1200 of FIG. 1. In an implementation, the outer layer 8100, the PCBA layer 8200, and the inner layer 8300 may be flexi-rigid. In an implementation, the outer layer 8100, the PCBA layer 8200, and the inner layer 8300 may be flexible.

In an implementation, the outer layer 8100 of the vital signs monitoring ring with integrated display 8000 may include a display area 8110. In an implementation, the display area 8110 may be a 3-digit, for example. In an implementation, the display area 8110 may have more or less digits. In an implementation, the display area 8110 may be a printed display. In an implementation, the display area 8110 may be a printed LED display implemented using organic, electrochromic, or quantum dot display techniques and materials as described herein. In an implementation, the display area 8110 may display oxygen saturation, pH levels, temperature, heart rate, and other physiological parameters. In an implementation, the display area 8110 may include step counts and other action-related parameters. In an implementation, the display area 8110 may include multiple display areas, where each display area may display a different physiological or action-related parameter.

In an implementation, the outer layer 8100 of the vital signs monitoring ring with integrated display 8000 may include a first electrode of a pair of printed silver-silver chloride (Ag—AgCl) electrodes for an ECG sensor measurements or for other sensor measurements. In an implementation, the first electrode is a screen-printed silver-silver chloride (Ag—AgCl) electrode which is touchable or engageable by a user to complete a sensor circuit with a second electrode. In an implementation, the outer layer 8100 of the vital signs monitoring ring with integrated display 8000 may include a power button to turn on the vital signs monitoring ring with integrated display 8000.

In an implementation, PCBA layer 8200 of the vital signs monitoring ring with integrated display 8000 may include a power source, passive and active electronics, sensors, and the like as described herein. The PCBA layer 8200 of the vital signs monitoring ring with integrated display 8000 may be electrically and mechanically connected to the outer layer 8100 of the vital signs monitoring ring with integrated display 8000. In an implementation, the power source may be a stack of Lithium polymer or similar batteries providing 3.6 V and 50 mAh, for example. In an implementation, the power source may be a flexible battery. The power source provides power to the various components on the vital signs monitoring ring with integrated display 8000.

In an implementation, the inner layer 8300 of the vital signs monitoring ring with integrated display 8000 may include the transmission mode oximetry measurement sensor components 8310 which may include LEDs 8320 and photodiodes 8330 and function as described herein. The LEDs 8320 may be red LEDs, near infrared (NIR) LEDs, and/or green LEDs. In an implementation, the LEDs 8320 and photodiodes 8330 may be implemented using electrochromic, organic or quantum dot materials and techniques. In an implementation, the inner layer 8300 of the vital signs monitoring ring with integrated display 8000 may include the second electrode of the pair of printed Ag—AgCl electrodes for the ECG sensor measurements or for other sensor measurements. In an implementation, the second electrode contacts a user surface when the vital signs monitoring ring with integrated display 8000 is positioned on the user digit. In an implementation, the second electrode contacts the user surface via a hydrogel layer. The inner layer 8300 of the vital signs monitoring ring with integrated display 8000 may be electrically and mechanically connected to the PBCA layer 8200 of the vital signs monitoring ring with integrated display 8000.

Oximeters sense oxygen saturation in tissues by optically quantifying concentrations of oxyhemoglobin ($HbO_2$) and deoxyhemoglobin (Hb). Pulse oximetry is one modality for ratiometric optical measurements on pulsatile arterial blood by leveraging photoplethysmography (PPG) at a minimum of two distinct wavelengths. PPG comprises optoelectronic components such as LEDs and photodiodes. In an implementation, the transmission mode oximetry measurement components may use red and NIR LEDs or red and green LEDs. The molar absorption coefficients of $HbO_2$ and Hb are disparate at the red and NIR wavelengths. The red LEDs and the NIR LEDs act as emitters (converting electrical energy into light energy) where light is transmitted at 612 nm and 712 nm wavelengths, respectively. In an implementation, red and green (532 nm) may also be used as LED combinations.

The photodiodes sense the non-absorbed light from the LEDs. The signals are inverted by means of an operational amplifier. These signals are interpreted as light that has been absorbed by the tissue being probed and are assigned to direct current (DC) and alternating current (AC) components. The DC component is treated as light absorbed by the tissue, venous blood, and non-pulsatile arterial blood. The AC component is treated as pulsatile arterial blood.

Figures 11A, 11B:
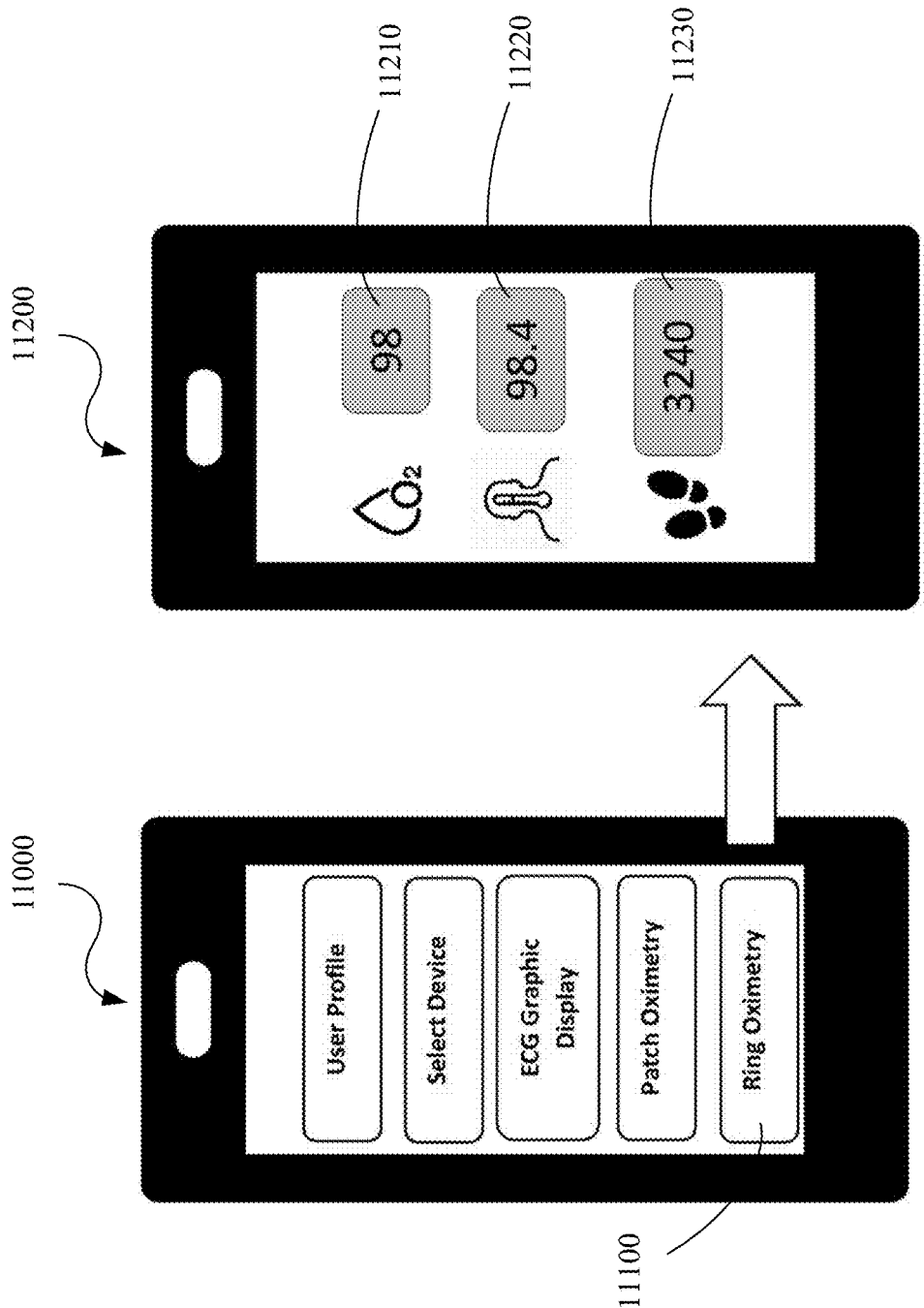
FIGS. 11A-B are example diagrams of an interface screen on a device for interacting with a vital signs monitoring ring with integrated display in accordance with certain implementations.

In an implementation, the data may be streamed to a device application through a Bluetooth® connection. FIGS. 11A-B are an example diagram of an interface screen 11000 on a device for interacting with a vital signs monitoring ring with integrated display in accordance with certain implementations. The interface screen 11000 may have a link or tab 11100 for selection of a sub-menu for ring oximetry display 11200. The ring oximetry display 11200 may show, for example, $SpO_2$, 11210, temperature 11230, step count 11220, and other physiological or action parameters.

As referenced herein above, the vital signs monitoring ring with integrated display may also include an application which may run on a device such as mobile devices, end user devices, cellular telephones, Internet Protocol (IP) devices, mobile computers, laptops, handheld computers, PDAs, personal media devices, smartphones, notebooks, notepads, phablets, smart watches, and the like (collectively "user device"). The vital signs monitoring ring with integrated display may wirelessly communicate with the user device and the application together with the user device may analyze, display and provide alerts to a user the vitals signs data collected by the vital signs monitoring ring with integrated display. The vital signs monitoring ring with integrated display may interface with the application to measure, stream and record real-time data for providing comprehensive sensing information to user(s). FIGS. 11A-B are example diagrams of interface screens for reviewing the sensor data as described herein.

Figure 9:
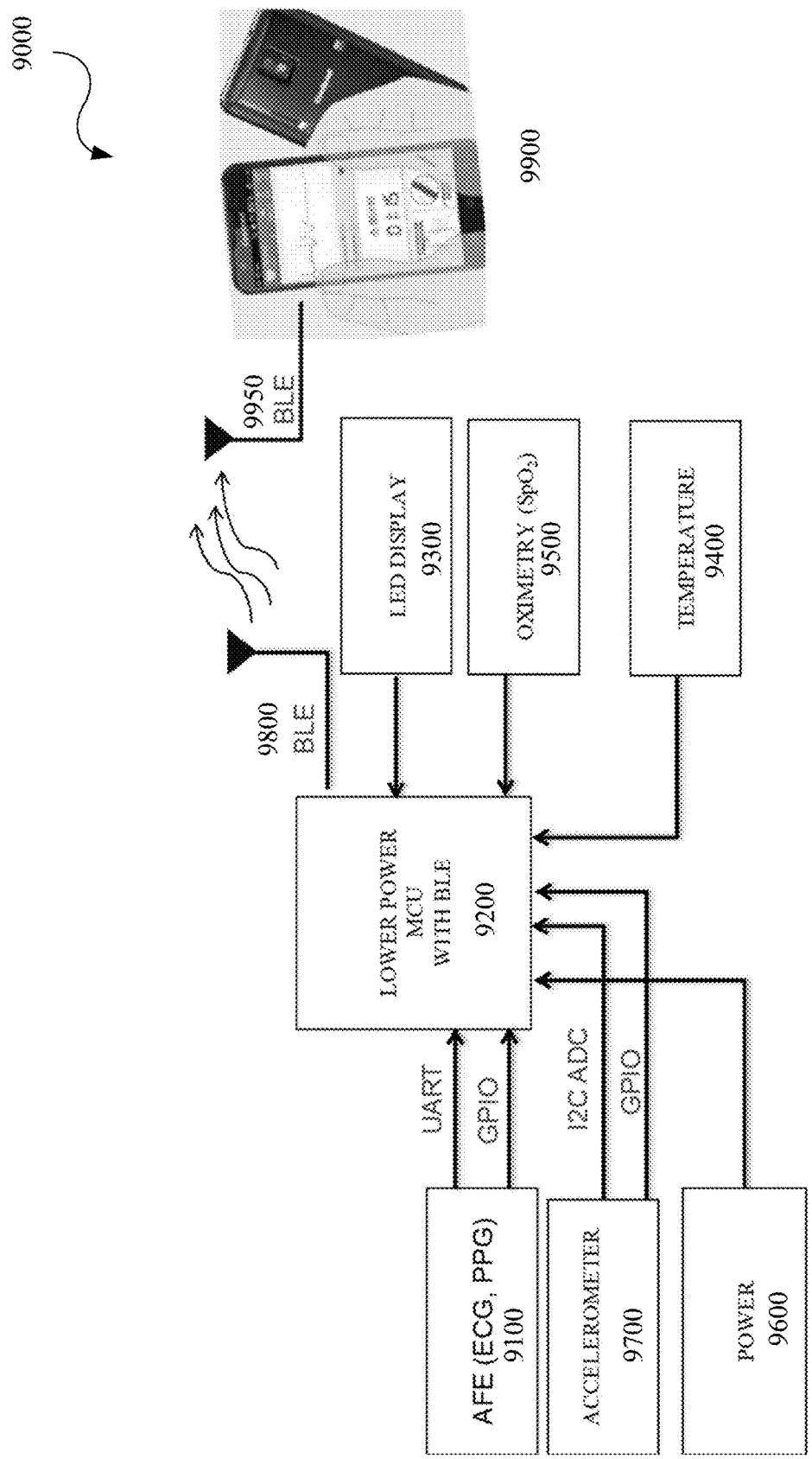
FIG. 9 is an example diagram of a hardware architecture of a vital signs monitoring ring with integrated display in accordance with certain implementations.

FIG. 9 is an example diagram of a hardware architecture of a vital signs monitoring ring with integrated display 9000 in accordance with certain implementations. The vital signs monitoring ring with integrated display 9000 includes an analog front-end (AFE) 9100 which may be connected to a variety of sensors present on the vital signs monitoring ring with integrated display 9000. The AFE 9100 may be connected to a processor 9200, which is further connected to a LED display 9300, temperature sensor(s) 9400, oximetry sensor 9500, power 9600, accelerometer 9700, and an antenna 9800. In an implementation, the processor 9200 is a low power MCU with integrated Bluetooth®. In an implementation, the antenna 9800 is a Bluetooth® which may communicate with a device 9900 using a corresponding antenna 9950. In an implementation, the hardware architecture may, in part, be implemented on the PCBA layer 1100, the PCBA layer 8200, and the like.

Figure 10:
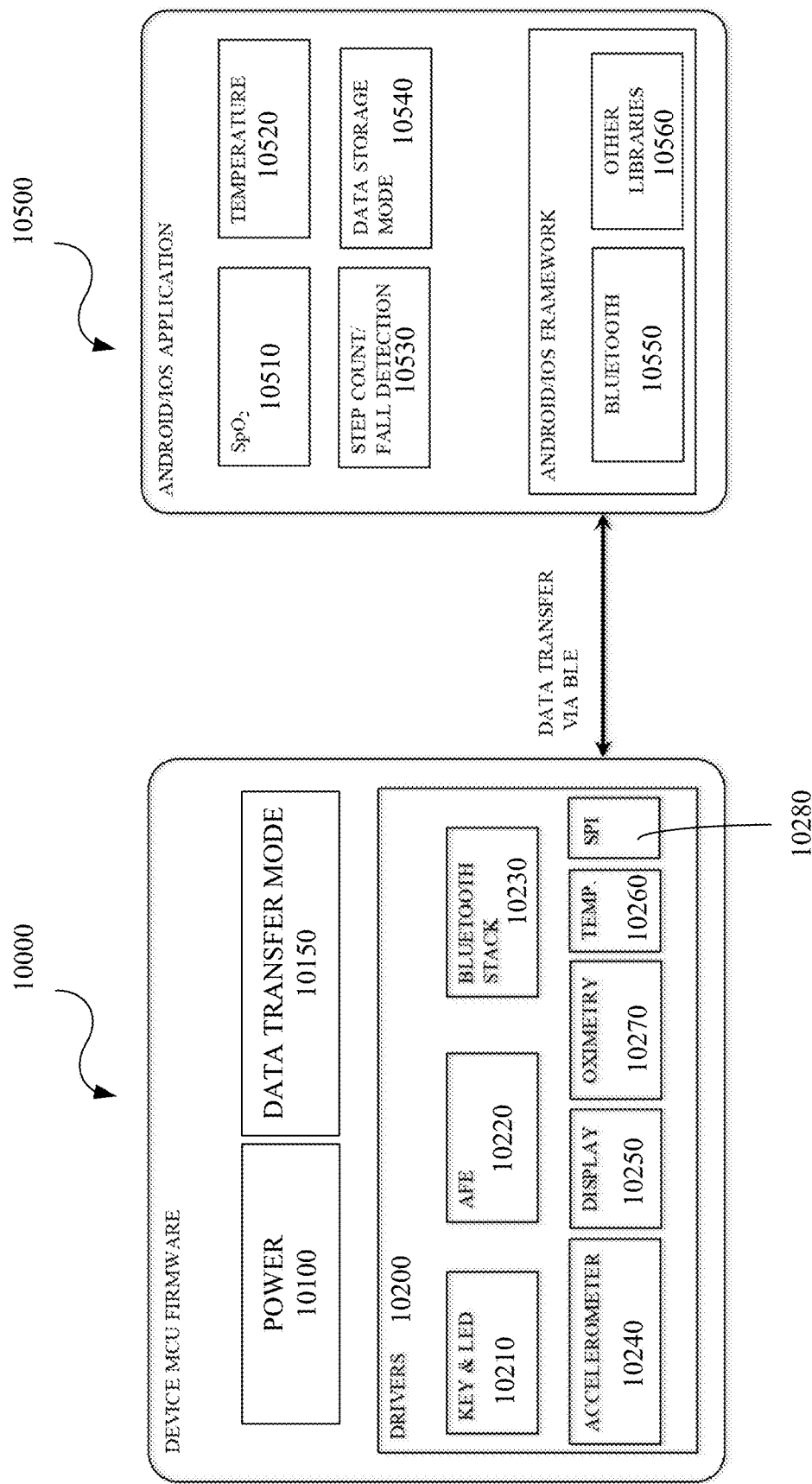
FIG. 10 is an example diagram of a software architecture of a vital signs monitoring ring with integrated display in accordance with certain implementations.

FIG. 10 is an example diagram of a software architecture of a vital signs monitoring ring with integrated display 10000 in accordance with certain implementations. A processor software/firmware of the vital signs monitoring ring with integrated display 10000 includes, but is not limited to, a power module 10100, a data transfer module 10150, and drivers 10200 for the LEDs 10210, AFE 10220, Bluetooth® stack 10230, accelerometer 10240, display 10250, temperature sensor 10260, oximetry 10270, serial peripheral interface 10280, and the like. An application device 10500 may include, but is not limited to, applications to process and display $SpO_2$ data 10510, temperature 10520, step count/fall detection (via accelerometer) 10530, and like data. The application device further includes a data storage mode 10540, a Bluetooth® stack 10550, and other libraries 10560. In an implementation, the software/firmware architecture may, in part, be implemented on or with the processor 9200.

Figure 12:
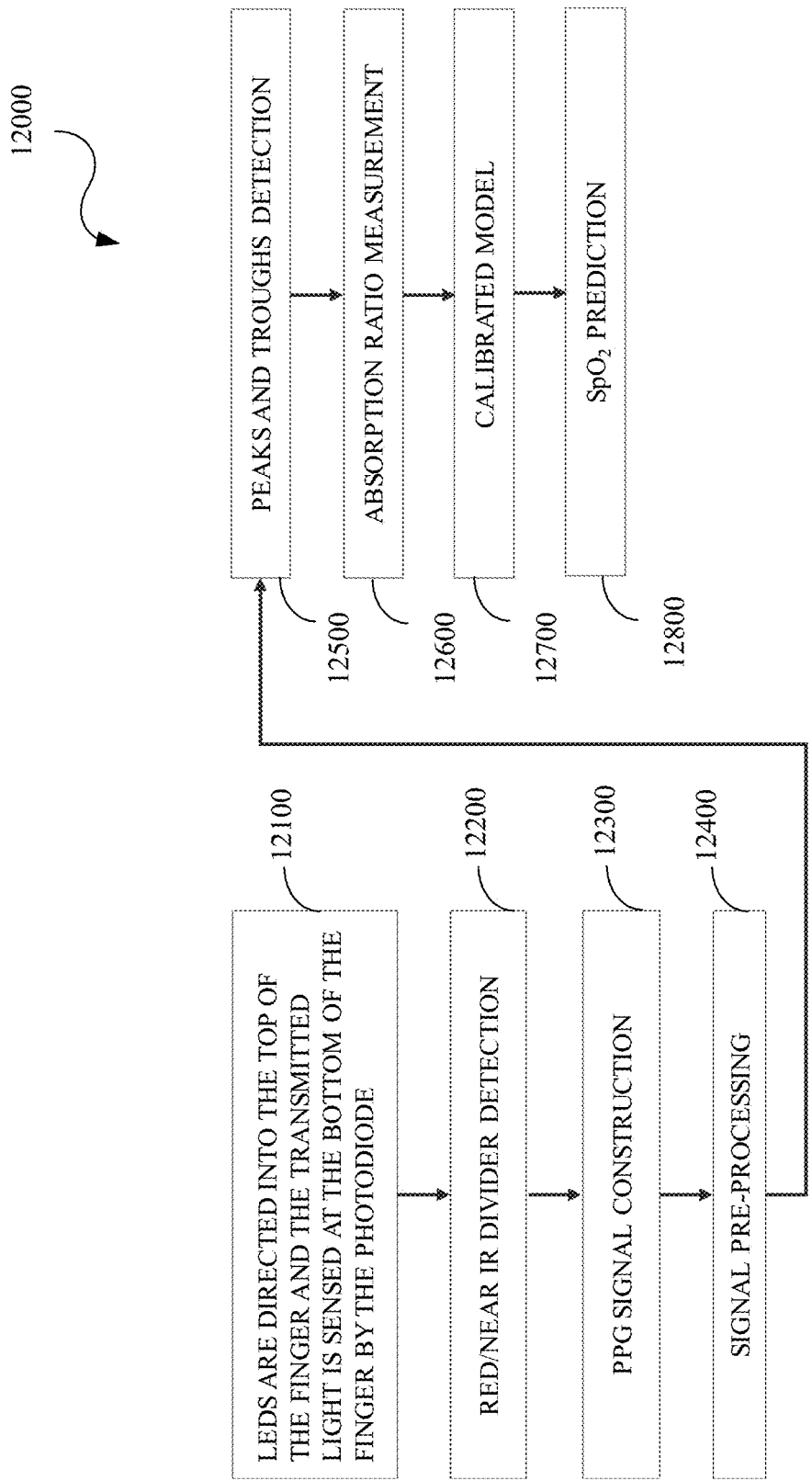
FIG. 12 is a flowchart for transmission mode oximetry measurement for a vital signs monitoring ring with integrated display in accordance with certain implementations.

FIG. 12 is a flowchart for a method 12000 for transmission mode oximetry measurement for a vital signs monitoring ring with integrated display in accordance with some implementations. The method 12000 includes: directing 12100 light from LEDs at user digit and sensing transmitted light at photodiodes; detecting 12200 specific wavelengths; generating 12300 $SpO_2$ signal; pre-processing 12400 the generated $SpO_2$ signal; detecting 12500 signal characteristics of the pre-processed $SpO_2$ signal; making 12600 absorption ratio measurements; applying 12700 absorption ratio measurements against calibration model; and predicting 12800 $SpO_2$ level.

The method 12000 includes directing 12100 light from LEDs at user digit and sensing transmitted light at photodiodes. The vital signs monitoring ring with integrated display may be positioned on a digit of a user. Upon activation, the LEDs transmit or emit light through the user digit. The photodiodes sense or capture the transmitted light as it travels through the user digit. In an implementation, red and NIR LEDs are used. In an implementation, red and green LEDs are used.

The method 12000 includes detecting 12200 specific wavelengths. Signals associated with specific wavelengths are separated or filtered from the captured transmitted light. In an implementation, red and NIR wavelengths are filtered. In an implementation, red and green wavelengths are filtered.

The method 12000 includes generating 12300 $SpO_2$ signal and pre-processing 12400 the generated $SpO_2$ signal. A $SpO_2$ signal is generated from the filtered wavelength signals and digital signal processing is applied to the $SpO_2$ signal.

The method 12000 includes detecting 12500 signal characteristics of the pre-processed $SpO_2$ signal. Signal characteristics determinative for $SpO_2$ are determined, such as, but not limited to, valleys and peaks of the processed $SpO_2$ signal.

The method 12000 includes making 12600 absorption ratio measurements. Absorption ratio measurements are computed from the $SpO_2$ signal characteristics.

The method 12000 includes applying 12700 absorption ratio measurements against calibration model. The absorption ratio measurements are normalized or calibrated against a model.

The method 12000 includes predicting 12800 $SpO_2$ level. The calibrated absorption ratio measurements are used to predict a $SpO_2$ level.

Figure 13:
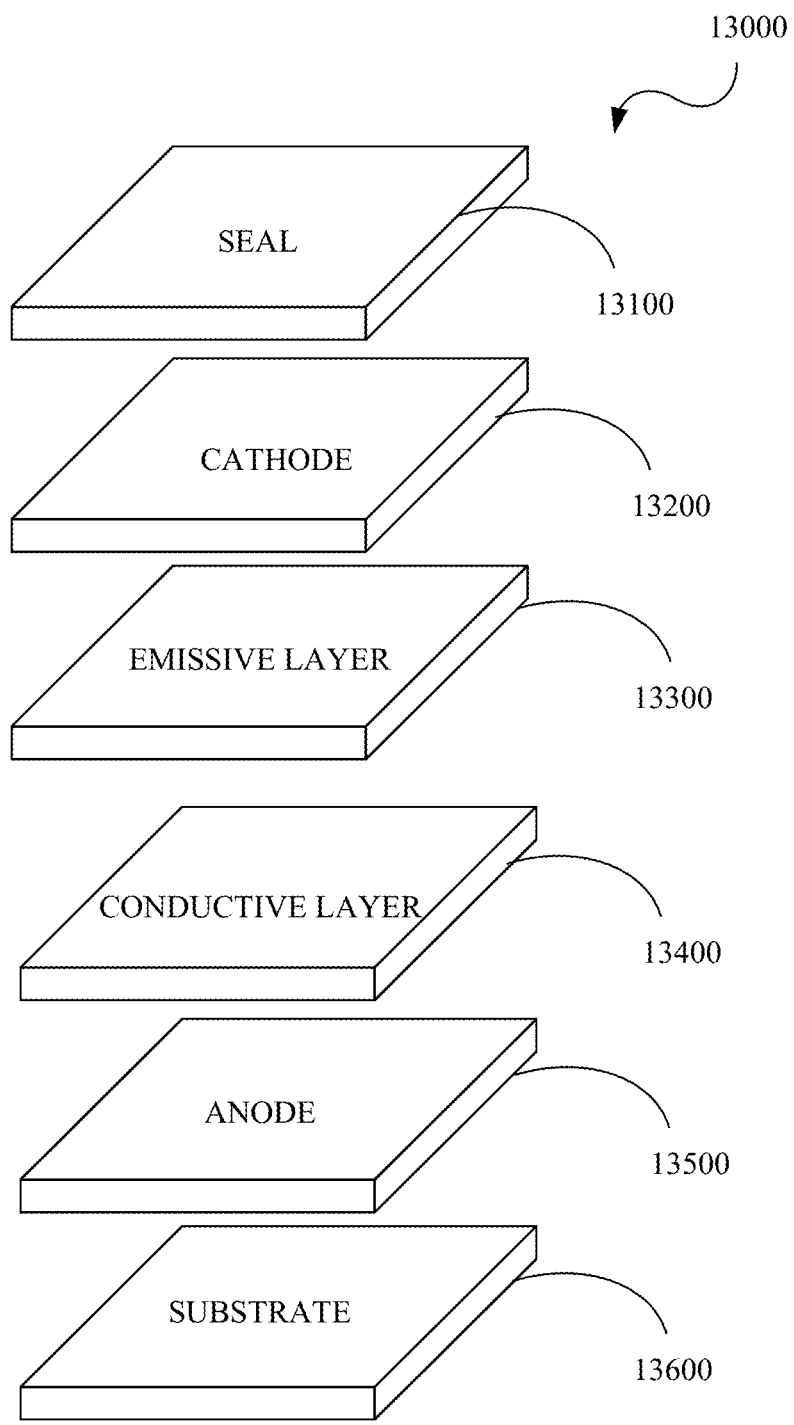
FIG. 13 is a diagram of an example display architecture for a vital signs monitoring ring with integrated display in accordance with certain implementations.

FIG. 13 is a diagram of an example Organic Light Emitting Diode (OLED) stack 13000 for a vital signs monitoring ring with integrated display in accordance with certain implementations. The OLED stack 13000 may include a seal layer 13100, a cathode layer 13200, an emissive layer 13300, a conductive layer 13400, an anode layer 13500, and a substrate 13600. In an implementation, the emissive layer 13300 may be a film of organic compound which emits light in response to current injection. The organic compound may be organic polymers, inks, light emitting polymers, and the like. In an implementation, the conductive layer 13400 may be organic polymers, inks, and the like.

Figure 14:
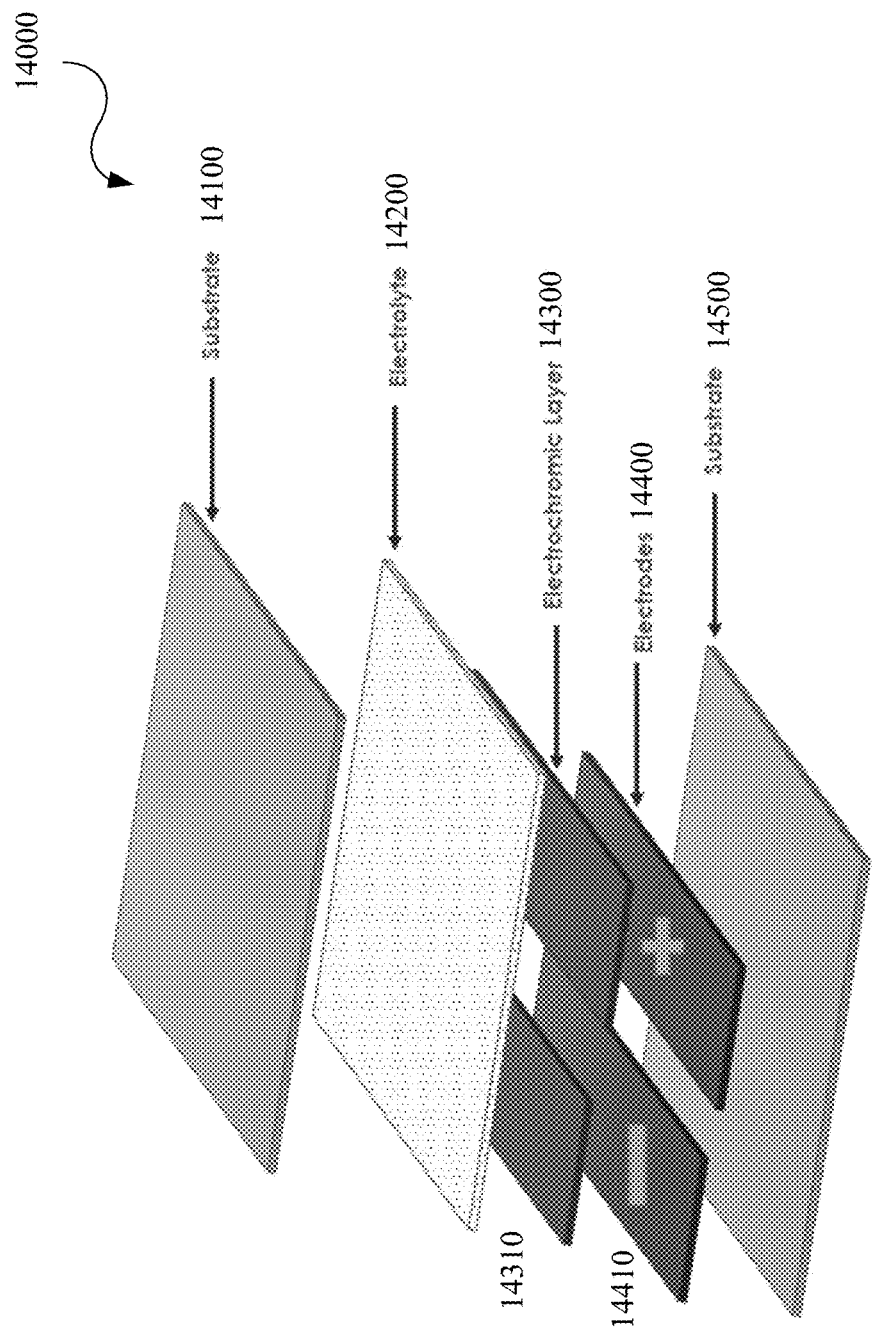
FIG. 14 is a diagram of an example display architecture for a vital signs monitoring ring with integrated display in accordance with certain implementations.

FIG. 14 is a diagram of an example Electrochromic Device (ECD) stack 14000 for a vital signs monitoring ring with integrated display in accordance with certain implementations. The ECD stack may include a substrate 14100, an electrolyte layer 14200, electrochromic layers 14300 and 14310, electrodes 14400 and 14410, and a substrate 14500. In this instance, the electrochromic materials are organic or inorganic substances that change color when charged with electricity. The ECD controls optical properties, such as transmission, absorption, reflectance and/or emittance, in a continual but reversible manner by applying voltage. The ECDs may be printed on plastics, paper, and the like and provide flexible yet robust structures. The ECDs use ultra-low power and are activated by small currents. The ECDs can be integrated with sensors for motion, touch, proximity, temperature and the like.

Figure 15A:
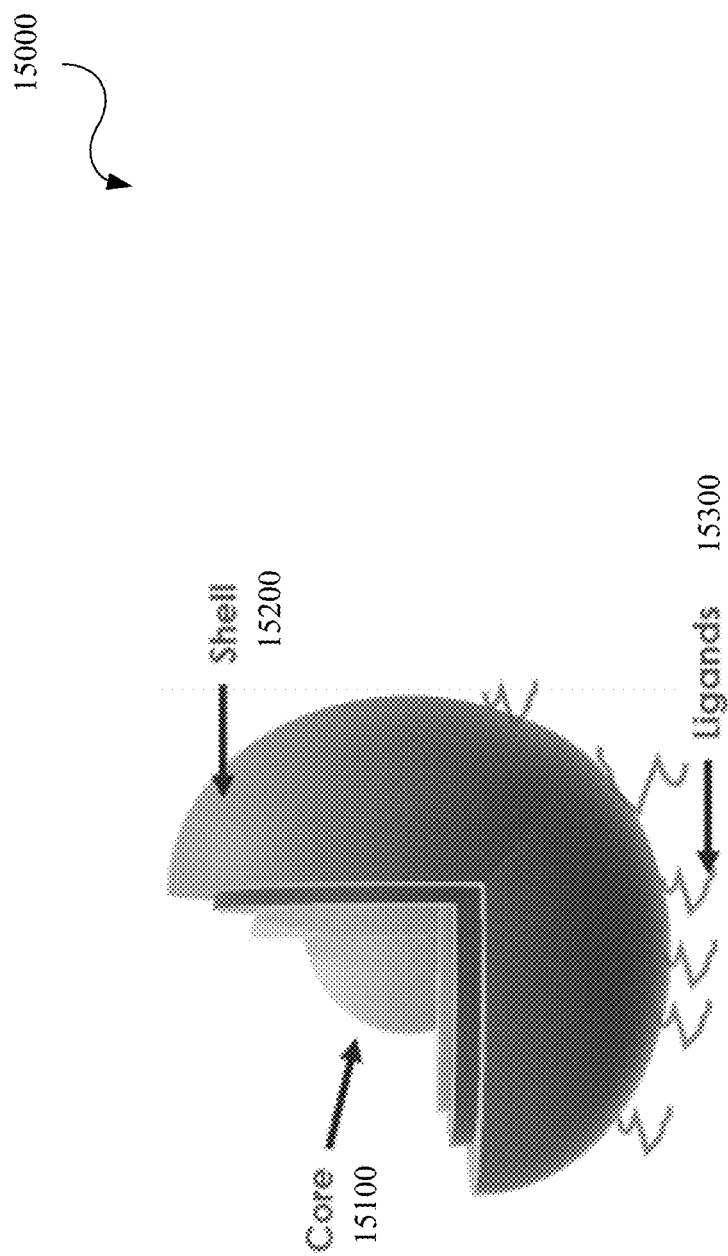
FIGS. 15A and 15 B are diagrams of an example display architecture for a vital signs monitoring ring with integrated display in accordance with certain implementations.
Figure 15B:
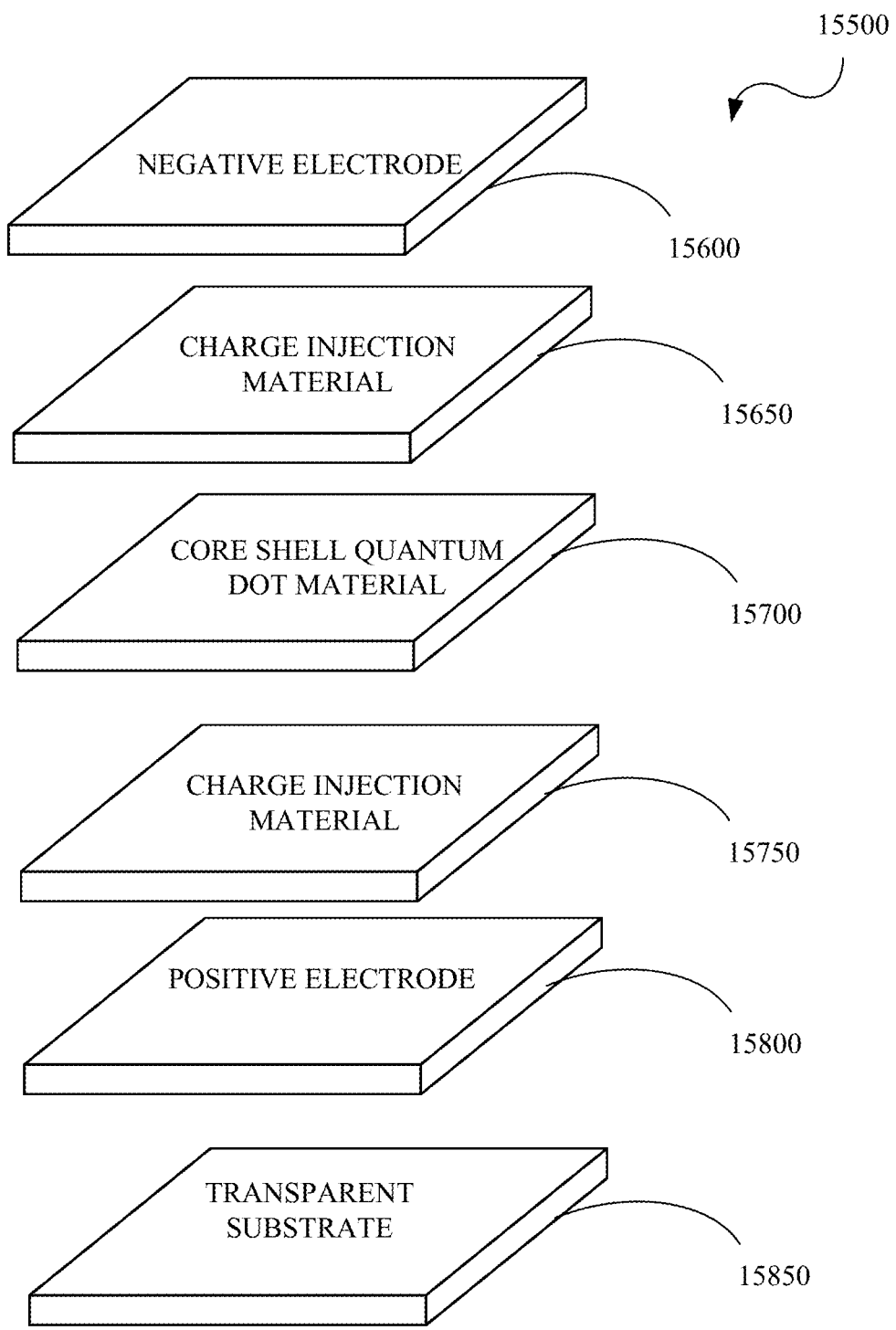

FIGS. 15A and 15B are architectures for quantum dot light emitting diodes (QLEDs). FIG. 15A is a diagram of a quantum dot 15000, which are semiconductor particles with optical and electrical properties in the nanometer size area. The quantum dot 15000, in general, includes a core 15100, a shell 15200 and ligands 15300. The core 15100 are the material emitting colors, the shell 15200 are coatings to protect the core 15100, and the ligands 15300 are long chain molecules so that the quantum dots can be printed in a liquid form.

FIG. 15B is a diagram of a QLED stack 15500 for a vital signs monitoring ring with integrated display in accordance with certain implementations. The QLED stack 15500 includes a negative voltage electrode 15600, a charge injection material layer 15650, a core-shell quantum dot layer 15700, a charge injection layer 15750, a positive voltage electrode 15800, and a transparent substrate 15850. The QLEDs produce pure monochromatic light (red, green, blue) and have low power consumption. Charge injected in the QLED stack 15500 results in electroluminescence. The chemical make-up and size of the quantum dots allows tuning of the color of the emitted light.

In general, a vital signs monitoring ring with integrated display includes a ring housing, the ring housing comprising at least two windows and a printed circuit board assembly (PCBA) layer configured to be attached to the ring housing. The PCBA layer includes a display section, a sensor section, a transmission mode oximetry measurement section configured to be in alignment with the at least two windows, a power supply, and a switch configured to power on the vital signs monitoring ring with integrated display via the power supply. The display section is configured to display physiological and action parameters associated with a user by sensing the physiological and action signals from a digit of user wearing the vital signs monitoring ring with integrated display using at least the sensor section and the transmission mode oximetry measurement section.

In an implementation, the sensor section includes at least one of an accelerometer, electrocardiogram (ECG) sensor, a temperature sensor, and a pH sensor. In an implementation, the PCBA layer further includes a first printed silver-silver chloride electrode printed on a top surface of the PCBA layer, a second printed silver-silver chloride electrode printed on a bottom surface of the PCBA layer, and a hydrogel layer connected to the second printed silver-silver chloride electrode, where the second printed silver-silver chloride electrode contacts a user digit through a third window when the vital signs monitoring ring with integrated display is positioned on the digit, and where a sensor circuit is completed with the second printed silver-silver chloride electrode when the user touches the first printed silver-silver chloride electrode. In an implementation, the transmission mode oximetry measurement components further includes first wavelength light emitting diodes configured to transmit light at the digit, second wavelength light emitting diodes configured to transmit light at the digit, and photodiodes configured to capture transmitted light traveling through the digit, where one of the first wavelength light emitting diodes and the second wavelength light emitting diodes, or the photodiodes are aligned in one window of the at least two windows and a remaining one of the first wavelength light emitting diodes and the second wavelength light emitting diodes, or the photodiodes are aligned in another window of the at least two windows. In an implementation, the PCBA layer further includes a wireless component which is configured to transmit at least sensor data to a monitoring device. In an implementation, the PCBA layer further includes a processor, the processor configured to filter the captured light signal to determine a first wavelength signal and a second wavelength signal, generate an oximetry signal from the first wavelength signal and the second wavelength signal, determine signal characteristics of the oximetry signal, determine absorption ratio measurements from the determined signal characteristics of the oximetry signal, calibrate the absorption ratio measurements, and predict an oximetry level. In an implementation, the ring housing further includes a charging port, the power source configured to be charged via the charging port.

In general, a vital signs monitoring ring with integrated display includes a first layer having a display section and an activation switch, a second layer having a sensor section and a power supply, and a third layer having an oximetry sensor. The first layer, the second layer, and the third layer are electrically and mechanically connected and collectively configured to be in a cylindrical configuration, where activation of the activation switch powers on the vital signs monitoring ring with integrated display via the power supply, and the display section is configured to display physiological and action parameters associated with a user by sensing the physiological and action signals from a digit of user wearing the vital signs monitoring ring with integrated display using at least the sensor section and the oximetry sensor.

In an implementation, the sensor section includes at least one of an accelerometer, electrocardiogram (ECG) sensor, a temperature sensor, and a pH sensor. In an implementation, the first layer includes a first printed silver-silver chloride electrode printed on a top surface of the first layer, the third layer includes a second printed silver-silver chloride electrode printed on a bottom surface of the third layer, and a hydrogel layer connected to the second printed silver-silver chloride electrode, where the second printed silver-silver chloride electrode contacts a user digit when the vital signs monitoring ring with integrated display is positioned on the digit, and where a sensor circuit is completed with the second printed silver-silver chloride electrode when the user touches the first printed silver-silver chloride electrode. In an implementation, the oximetry sensor include transmission mode oximetry measurement components further includes first wavelength light emitting diodes configured to transmit light at the digits, second wavelength light emitting diodes configured to transmit light at the digit, and photodiodes configured to capture transmitted light traveling through the digit. In an implementation, the oximetry sensor include reflective mode oximetry measurement components further includes photodiodes configured to capture transmitted light reflected from the digit. In an implementation, the ring further includes a ring shell, the ring shell configured to hold the first layer, the second layer, and the third layer. In an implementation, the ring shell further includes a charging port, the power source configured to be charged via the charging port. In an implementation, the second layer further comprises a processor, the processor configured to filter the captured light signal to determine a first wavelength signal and a second wavelength signal, generate an oximetry signal from the first wavelength signal and the second wavelength signal, determine signal characteristics of the oximetry signal, determine absorption ratio measurements from the determined signal characteristics of the oximetry signal, calibrate the absorption ratio measurements, and predict an oximetry level.

In general, a vital signs monitoring ring with integrated display includes a display layer including a switch and a sensor layer including at least accelerometer, a temperature sensor, and a transmission mode oximetry sensor. The display layer and the sensor layer are electrically and mechanically connected and collectively configured to be in a cylindrical configuration, where activation of an activation switch powers on the vital signs monitoring ring with integrated display via a power supply, and the display section is configured to display sensor data associated with a user by sensing signals from a digit of user wearing the vital signs monitoring ring with integrated display using at least the accelerometer, the temperature sensor, and the transmission mode oximetry sensor.

In an implementation, the sensor section further includes at least one of an electrocardiogram (ECG) sensor and a pH sensor. In an implementation, the display layer includes a first printed silver-silver chloride electrode printed on a top surface of the display layer, the sensor layer includes a second printed silver-silver chloride electrode printed on a bottom surface of the sensor layer, and a hydrogel layer connected to the second printed silver-silver chloride electrode, where the second printed silver-silver chloride electrode contacts a user digit when the vital signs monitoring ring with integrated display is positioned on the digit, and where a sensor circuit is completed with the second printed silver-silver chloride electrode when the user touches the first printed silver-silver chloride electrode. In an implementation, the transmission mode oximetry sensor further includes first wavelength light emitting diodes configured to transmit light at the digit, second wavelength light emitting diodes configured to transmit light at the digit, and photodiodes configured to capture transmitted light traveling through the digit. In an implementation, the sensor layer further comprises a processor, the processor configured to filter the captured light signal to determine a first wavelength signal and a second wavelength signal, generate an oximetry signal from the first wavelength signal and the second wavelength signal, determine signal characteristics of the oximetry signal, determine absorption ratio measurements from the determined signal characteristics of the oximetry signal, calibrate the absorption ratio measurements, and predict an oximetry level.

The construction and arrangement of the methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials and components, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A vital signs monitoring ring with integrated display comprising:
    a ring housing, the ring housing comprising at least two windows; and
    a printed circuit board assembly (PCBA) layer configured to be attached to the ring housing, the PCBA layer comprising:
        a display section, wherein the display section is a printed display;
        a sensor section including a pH sensor;
        a transmission mode oximetry measurement section configured to be in alignment with the at least two windows;
        a reflective mode oximetry measurement section configured to work in combination with the transmission mode oximetry measurement section;
        a power supply; and
        a switch configured to power on the vital signs monitoring ring via the power supply,
    wherein the display section is configured to display physiological and action parameters associated with a user by sensing the physiological and action signals from a digit of the user wearing the vital signs monitoring ring using at least the sensor section and the transmission mode oximetry measurement section, and
    wherein the PCBA layer is further comprising:
        a first printed silver-silver chloride electrode printed on a top surface of the PCBA layer;
        a second printed silver-silver chloride electrode printed on a bottom surface of the PCBA layer; and
        a hydrogel layer connected to the second printed silver-silver chloride electrode,
        wherein the second printed silver-silver chloride electrode contacts the digit through a third window when the vital signs monitoring ring is positioned on the digit,
        wherein a sensor circuit is completed with the second printed silver-silver chloride electrode when the user touches the first printed silver-silver chloride electrode, and
        wherein the pH sensor is implemented using the first printed silver-silver chloride electrode and the second printed silver-silver chloride electrode.

2. The ring of claim 1, wherein the sensor section includes an accelerometer, electrocardiogram (ECG) sensor, and a temperature sensor.

3. The ring of claim 1, wherein the transmission mode oximetry measurement section are further comprising:
    first wavelength light emitting diodes configured to transmit light at the digit;
    second wavelength light emitting diodes configured to transmit light at the digit; and
    photodiodes configured to capture transmitted light traveling through the digit,
    wherein one of the first wavelength light emitting diodes and the second wavelength light emitting diodes, or the photodiodes, are aligned in one window of the at least two windows and a remaining one of the first wavelength light emitting diodes and the second wavelength light emitting diodes, or the photodiodes' are aligned in another window of the at least two windows.

4. The ring of claim 3, wherein the PCBA layer further includes a wireless component which is configured to transmit at least sensor data to a monitoring device.

5. The ring of claim 3, wherein the PCBA layer further comprises a processor, the processor configured to:
    filter the captured light signal to determine a first wavelength signal and a second wavelength signal;
    generate an oximetry signal from the first wavelength signal and the second wavelength signal;
    determine signal characteristics of the oximetry signal;
    determine absorption ratio measurements from the determined signal characteristics of the oximetry signal;
    calibrate the absorption ratio measurements; and
    predict an oximetry level.

6. The ring of claim 1, wherein the ring housing further includes a charging port, the power supply configured to be charged via the charging port.

7. A vital signs monitoring ring with integrated display comprising:
    a first layer having a printed display section and an activation switch;

a second layer having a sensor section and a power supply, wherein the sensor section includes a pH sensor; and a third layer having an oximetry sensor implemented using a transmissive oximeter and a reflective oximeter, wherein the first layer, the second layer, and the third layer are electrically and mechanically connected and collectively configured to be in a cylindrical configuration, wherein activation of the activation switch powers on the vital signs monitoring ring via the power supply, wherein the display section is configured to display physiological and action parameters associated with a user by sensing the physiological and action signals from a digit of the user wearing the vital signs monitoring ring using at least the sensor section and the oximetry sensor, and wherein:
the first layer includes a first printed silver-silver chloride electrode printed on a top surface of the first layer;
the third layer includes a second printed silver-silver chloride electrode printed on a bottom surface of the third layer; and
a hydrogel layer connected to the second printed silver-silver chloride electrode,
wherein the second printed silver-silver chloride electrode contacts the digit when the vital signs monitoring ring is positioned on the digit,
wherein a sensor circuit is completed with the second printed silver-silver chloride electrode when the user touches the first printed silver-silver chloride electrode, and
wherein the pH sensor is implemented using the first printed silver-silver chloride electrode and the second printed silver-silver chloride electrode.

8. The ring of claim 7, wherein the sensor section includes an accelerometer, electrocardiogram (ECG) sensor, and a temperature sensor.

9. The ring of claim 8, wherein the transmissive oximeter is further comprising:
first wavelength light emitting diodes configured to transmit light at the digit;
second wavelength light emitting diodes configured to transmit light at the digit; and
photodiodes configured to capture transmitted light traveling through the digit.

10. The ring of claim 9, wherein the reflective oximeter is further comprising:
photodiodes configured to capture transmitted light reflected from the digit.

11. The ring of claim 7, further comprising:
a ring shell, the ring shell configured to hold the first layer, the second layer, and the third layer.

12. The ring of claim 11, wherein the ring shell further includes a charging port, the power supply configured to be charged via the charging port.

13. The ring of claim 7, wherein the second layer further comprises a processor, the processor configured to:
filter the captured light signal to determine a first wavelength signal and a second wavelength signal;
generate an oximetry signal from the first wavelength signal and the second wavelength signal;
determine signal characteristics of the oximetry signal;
determine absorption ratio measurements from the determined signal characteristics of the oximetry signal;
calibrate the absorption ratio measurements; and
predict an oximetry level.

14. A vital signs monitoring ring with integrated display comprising:
a display layer including a switch and a printed display; and
a sensor layer including at least an accelerometer, a temperature sensor, a pH sensor, a reflective mode oximetry sensor, and a transmission mode oximetry sensor,
wherein the display layer and the sensor layer are electrically and mechanically connected and collectively configured to be in a cylindrical configuration,
wherein activation of the switch powers on the vital signs monitoring ring via a power supply,
wherein the display layer is configured to display sensor data associated with a user by sensing signals from a digit of the user wearing the vital signs monitoring ring using at least the accelerometer, the temperature sensor, and the transmission mode oximetry sensor, and
wherein:
the display layer includes a first printed silver-silver chloride electrode printed on a top surface of the display layer;
the sensor layer includes a second printed silver-silver chloride electrode printed on a bottom surface of the sensor layer; and
a hydrogel layer connected to the second printed silver-silver chloride electrode,
wherein the second printed silver-silver chloride electrode contacts the digit when the vital signs monitoring ring is positioned on the digit,
wherein a sensor circuit is completed with the second printed silver-silver chloride electrode when the user touches the first printed silver-silver chloride electrode, and
wherein the pH sensor is implemented using the first printed silver-silver chloride electrode and the second printed silver-silver chloride electrode.

15. The ring of claim 14, wherein the sensor layer further includes an electrocardiogram (ECG) sensor.

16. The ring of claim 14, wherein the transmission mode oximetry sensor is further comprising:
first wavelength light emitting diodes configured to transmit light at the digit;
second wavelength light emitting diodes configured to transmit light at the digit; and
photodiodes configured to capture transmitted light traveling through the digit.

17. The ring of claim 16, wherein the sensor layer further comprises a processor, the processor configured to:
filter the captured light signal to determine a first wavelength signal and a second wavelength signal;
generate an oximetry signal from the first wavelength signal and the second wavelength signal;
determine signal characteristics of the oximetry signal;
determine absorption ratio measurements from the determined signal characteristics of the oximetry signal;
calibrate the absorption ratio measurements; and
predict an oximetry level.

* * * * *